(12) United States Patent
Harmon et al.

(10) Patent No.: US 8,236,538 B2
(45) Date of Patent: Aug. 7, 2012

(54) METHODS FOR STERILIZING MATERIALS CONTAINING BIOLOGICALLY ACTIVE AGENTS

(75) Inventors: Alexander M. Harmon, Clinton, NJ (US); Laura J. Brown, Hamilton Square, NJ (US); Charles J. Buckle, Hillsborough, NJ (US); Frederick Halperin, Hillsborough, NJ (US); Stanko Bodnar, Whitehouse Station, NJ (US)

(73) Assignee: Advanced Technologies and Regenerative Medicine, LLC, Raynham, MA (US)

( * ) Notice: Subject to any disclaimer, the term of this patent is extended or adjusted under 35 U.S.C. 154(b) by 626 days.

(21) Appl. No.: 12/337,425

(22) Filed: Dec. 17, 2008

(65) Prior Publication Data

US 2009/0166178 A1 Jul. 2, 2009

Related U.S. Application Data

(60) Provisional application No. 61/015,350, filed on Dec. 20, 2007.

(51) Int. Cl.
*A61L 2/08* (2006.01)
(52) U.S. Cl. .................................. 435/173.7; 422/22
(58) Field of Classification Search .................. None
See application file for complete search history.

(56) References Cited

U.S. PATENT DOCUMENTS

| | | | |
|---|---|---|---|
| 4,352,883 A | 10/1982 | Lim | |
| 4,882,162 A | 11/1989 | Ikada et al. | |
| 4,963,489 A | 10/1990 | Naughton et al. | |
| 5,004,681 A | 4/1991 | Boyse et al. | |
| 5,192,553 A | 3/1993 | Boyse et al. | |
| 5,286,632 A | 2/1994 | Jones | |
| 5,320,962 A | 6/1994 | Stiles et al. | |
| 5,342,761 A | 8/1994 | MacLeod | |
| 5,365,737 A | 11/1994 | Moriya et al. | |
| 5,437,994 A | 8/1995 | Emerson et al. | |
| 5,443,950 A | 8/1995 | Naughton et al. | |
| 5,456,835 A | 10/1995 | Castino et al. | |
| 5,486,359 A | 1/1996 | Caplan et al. | |
| 5,580,777 A | 12/1996 | Bernard et al. | |
| 5,589,376 A | 12/1996 | Anderson et al. | |
| 5,670,483 A | 9/1997 | Zhang et al. | |
| 5,677,181 A | 10/1997 | Parish | |
| 5,730,933 A | 3/1998 | Peterson | |
| 5,811,094 A | 9/1998 | Caplan et al. | |
| 5,827,735 A | 10/1998 | Young et al. | |
| 5,834,308 A | 11/1998 | Peck et al. | |
| 5,840,580 A | 11/1998 | Terstappen et al. | |
| 5,842,477 A | 12/1998 | Naughton et al. | |
| 5,843,780 A | 12/1998 | Thomson | |
| 5,869,079 A | 2/1999 | Wong et al. | |
| 5,902,741 A | 5/1999 | Purchio et al. | |
| 5,906,934 A | 5/1999 | Grande et al. | |
| 5,919,702 A | 7/1999 | Purchio et al. | |
| 5,942,225 A | 8/1999 | Bruder et al. | |
| 5,962,325 A | 10/1999 | Naughton et al. | |
| 5,994,094 A | 11/1999 | Hötten et al. | |
| 6,001,647 A | 12/1999 | Peck et al. | |
| 6,022,743 A | 2/2000 | Naughton et al. | |
| 6,059,968 A | 5/2000 | Wolf | |
| 6,140,039 A | 10/2000 | Naughton et al. | |
| 6,153,591 A | 11/2000 | Cai et al. | |
| 6,200,606 B1 | 3/2001 | Peterson et al. | |
| 6,200,806 B1 | 3/2001 | Thomson | |
| 6,214,369 B1 | 4/2001 | Grande et al. | |
| 6,291,240 B1 | 9/2001 | Mansbridge et al. | |
| 6,323,188 B1 | 11/2001 | Weissman | |
| 6,326,201 B1 | 12/2001 | Fung et al. | |
| 6,331,313 B1 | 12/2001 | Wong et al. | |
| 6,333,029 B1 | 12/2001 | Vyakarnam et al. | |
| 6,355,239 B1 | 3/2002 | Bruder et al. | |
| 6,355,699 B1 | 3/2002 | Vyakarnam et al. | |
| 6,358,737 B1 | 3/2002 | Bonewald et al. | |
| 6,366,149 B1 | 4/2002 | Lee et al. | |
| 6,372,494 B1 | 4/2002 | Naughton et al. | |
| 6,387,367 B1 | 5/2002 | Davis-Sproul et al. | |
| 6,391,297 B1 | 5/2002 | Halvorsen | |
| 6,429,013 B1 | 8/2002 | Halvorsen et al. | |
| 6,436,704 B1 | 8/2002 | Roberts et al. | |
| 6,497,875 B1 | 12/2002 | Sorrell et al. | |
| 6,528,245 B2 | 3/2003 | Sanchez-Ramos et al. | |
| 6,534,084 B1 | 3/2003 | Vyakarnam et al. | |
| 6,555,374 B1 | 4/2003 | Gimble et al. | |
| 6,599,323 B2 | 7/2003 | Melican et al. | |

(Continued)

FOREIGN PATENT DOCUMENTS

EP 1 216 718 6/2002

(Continued)

OTHER PUBLICATIONS

In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.

(Continued)

*Primary Examiner* — Jim Ketter
(74) *Attorney, Agent, or Firm* — Venable LLP; Toni-Junell Herbert; Therese M. Finan

(57) ABSTRACT

Provided are methods for sterilizing a material comprising a biologically-active agent comprising irradiating said material with ionizing radiation at a dose of about 5 kGy to about 25 kGy while maintaining said material in an atmosphere comprising at least 95% by volume inert gas and at a temperature of about 4° C. or lower. Also provided are sterilized materials comprising a biologically-active agent, wherein said materials exhibit substantially the same amount of biological activity as a non-sterilized control.

28 Claims, 5 Drawing Sheets

U.S. PATENT DOCUMENTS

| | | |
|---|---|---|
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,696,060 B2 * | 2/2004 | Grieb et al. ............... 424/176.1 |
| 6,703,017 B1 | 3/2004 | Peck et al. |
| 6,916,655 B2 | 7/2005 | Yasumoto et al. |
| 7,871,654 B2 * | 1/2011 | Byun et al. .................... 426/234 |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0064000 A1 * | 4/2003 | Burgess et al. ............... 422/22 |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0124721 A1 | 7/2003 | Cheatham et al. |
| 2003/0138948 A1 | 7/2003 | Fisk et al. |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0101958 A1 | 5/2004 | Shimp |
| 2004/0136967 A1 | 7/2004 | Weiss et al. |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0148074 A1 | 7/2005 | Davies et al. |
| 2005/0249731 A1 | 11/2005 | Aslan et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0264269 A1 | 11/2007 | Harmon et al. |
| 2007/0275362 A1 | 11/2007 | Edinger et al. |
| 2008/0112939 A1 | 5/2008 | Colter et al. |
| 2008/0145934 A1 | 6/2008 | Harris et al. |
| 2008/0166328 A1 | 7/2008 | Harmon et al. |

FOREIGN PATENT DOCUMENTS

| | | |
|---|---|---|
| EP | 1 405 649 | 4/2004 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 96/01316 | 1/1996 |
| WO | WO 96/05309 | 2/1996 |
| WO | WO 98/17791 | 4/1998 |
| WO | WO 98/33515 | 8/1998 |
| WO | WO 98/51317 | 11/1998 |
| WO | WO 99/03973 | 1/1999 |
| WO | WO 99/28444 | 6/1999 |
| WO | WO 00/09666 | 2/2000 |
| WO | WO 00/38762 | 7/2000 |
| WO | WO 00/06351 | 8/2000 |
| WO | WO 00/73421 | 12/2000 |
| WO | WO 01/11011 | 2/2001 |
| WO | WO 01/19379 | 3/2001 |
| WO | WO 01/34775 | 5/2001 |
| WO | WO 02/036751 | 5/2002 |
| WO | WO 02/046373 | 6/2002 |
| WO | WO 02/059278 | 8/2002 |
| WO | WO 02/061053 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |

| | | |
|---|---|---|
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 2004/011012 | 2/2004 |
| WO | WO 2004/011621 | 2/2004 |
| WO | WO 2004/016747 | 2/2004 |
| WO | WO 2004/023100 | 3/2004 |
| WO | WO 2004/072273 | 8/2004 |
| WO | WO 2005/001076 | 1/2005 |
| WO | WO 2005/001077 | 1/2005 |
| WO | WO 2005/001078 | 1/2005 |
| WO | WO 2005/001079 | 1/2005 |
| WO | WO 2005/001080 | 1/2005 |
| WO | WO 2005/003334 | 1/2005 |
| WO | WO 2005/021738 | 3/2005 |
| WO | WO 2005/038012 | 4/2005 |
| WO | WO 2006/036826 | 4/2006 |
| WO | WO 2006/071773 | 7/2006 |
| WO | WO 2006/071777 | 7/2006 |
| WO | WO 2006/071778 | 7/2006 |
| WO | WO 2006/071794 | 7/2006 |
| WO | WO 2006/071802 | 7/2006 |
| WO | WO 2006/105152 | 10/2006 |
| WO | WO 2007/073552 | 6/2007 |
| WO | WO 2007/108003 | 9/2007 |
| WO | WO 2008/045498 | 4/2008 |
| WO | WO 2008/060541 | 5/2008 |

OTHER PUBLICATIONS

In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U.S. Patent and Trademark Office, Non-Final Office Action in re: U.S. Appl. No. 11/322,372, dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.

In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the United States Patent and Trademark Office, Final Office Action in re: U.S. Appl. No. 11/315,898, dated Sep. 16, 2008, 13 pages.
In the United States Patent and Trademark Office, Non-Final Office Action in re: U.S. Appl. No. 11/323,372, dated Sep. 3, 2008, 45 pages.
In the United States Patent and Trademark Office, Non-Final Office Action in re: U.S. Appl. No. 11/317,574, dated Sep. 30, 2008, 28 pages.
In the U. S. Patent and Trademark Office, Non-Final Office Action in re: U.S. Appl. No. 11/315,969, dated Dec. 23, 2008, 18 pages.
In the U. S. Patent and Trademark Office, Non-Final Office Action in re: U.S. Appl. No. 10/951,357, dated Nov. 26, 2008, 25 pages.
In the U. S. Patent and Trademark Office, Non-Final Office Action in re: U.S. No. 11/321,864, dated Jan. 8, 2009, 34 pages.
In the U. S. Patent and Trademark Office, Non-Final Office Action in re: U.S. Appl. No. 11/315,943, dated Feb. 20, 2009, 17 pages.
In the U. S. Patent and Trademark Office, Non-Final Office Action in re: U.S. Appl. No. 11/611,602, dated Mar. 3, 2009, 18 pages.
In the U. S. Patent and Trademark Office, Non-Final Office Action in re: U.S. Appl. No. 11/297,778, dated Mar. 9, 2009, 12 pages.
In the U. S. Patent and Trademark Office, Non-Final Office Action in re: U.S. Appl. No. 11/481,481, dated Mar. 20, 2009, 48 pages.
In the U. S. Patent and Trademark Office, Final Office Action in re: U.S. Appl. No. 11/315,897, dated Mar. 20, 2009, 21 pages.
In the U. S. Patent and Trademark Office, Non-Final Office Action in re: U.S. Appl. No. 11/481,480, dated Mar. 20, 2009, 50 pages.
In the U. S. Patent and Trademark Office, Final Office Action in re: U.S. Appl. No. 11/321,863, dated Feb. 12, 2009, 24 pages.
In the U. S. Patent and Trademark Office, Final Office Action in re: U.S. Appl. No. 11/322,003 dated Feb. 13, 2009, 24 pages.
In the U. S. Patent and Trademark Office, Final Office Action in re: U.S. Appl. No. 10/876,998 dated Feb. 13, 2009, 18 pages.
In the U. S. Patent and Trademark Office, Final Office Action in re: U.S. Appl. No. 11/322,372 dated Feb. 13, 2009, 22 pages.
In the U. S. Patent and Trademark Office, Non-Final Office Action in re: U.S. Appl. No. 11/304,091 dated Feb. 27, 2009, 36 pages.
In the U. S. Patent and Trademark Office, Non-Final Office Action in re: U.S. Appl. No. 11/481,456 dated Apr. 16, 2009, 50 pages.
In the U. S. Patent and Trademark Office, Non-Final Office Action in re: U.S. Appl. No. 10/877,445, dated Mar. 19, 2009, 23 pages.
In the U. S. Patent and Trademark Office, Non-Final Office Action in re: U.S. Appl. No. 11/317,574 dated Apr. 29, 2009, 29 pages.

Aboody, K.S. et al., "Neural Stem Cells Display Extensive Tropism for Pathology in Adult Brain: Evidence From Intracranial Gliomase," PNAS, 2000; 97(23):12846-51.

Agbulut, O. et al., "Comparison of Human Skeletal Myoblasts and Bone Marrow-Derived CD133+ Progenitors for the Repair of Infarcted Myocardium," Journal of the American College of Cardiology, 2004; 44(2):458-63.

Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss," AREDS Report No. 8, Arch. Opthalmol., 2001; 119:1417-36.

Aggarwal et al., "Human Mesenchymal Stem Cells Modulate Allogeneic Immune Cell Responses," Blood, 2005; 105(4):1815-1822.

Aldskogius, H. et al., "Strategies for Repair of the Deafferented Spinal Cord," Brain Res. Rev., 2002; 40:301-08.

Allcock, H.R. et al., "Synthesis of Poly[(Amino Acid Alkyl Ester)Phosphazenes]1-3," Macromolecules, 1977; 10(4):824-830.

Altman, G.H. et al., "Advanced Bioreactor With Controlled Application of Multi-Dimensional Strain for Tissue Engineering," J. Biomech. Eng., 2002; 124:742-749.

Altman, R.D. et al., "Radiographic Assessment of Progression in Osteoarthritis," Arthritis & Rheum., 1987; 30(11):1214-25.

Anseth, K.S. et al., "In Situ Forming Degradable Networks and Their Application in Tissue Engineering and Drug Delivery," J. of Controlled Release, 2002; 78:199-209.

Armulik, A. et al., "Endothelial/Pericyte Interactions," Circ. Res., 2005; 97:512-23.

Auda-Boucher, G. et al., "Staging of the Commitment of Murine Cardiac Cell Progenitors," Dev. Bio., 2000; 225(1):214-25.

Avital, I. et al., "Isolation, Characterization, and Transplantation of Bone Marrow-Derived Hepatocyte Stem Cells," Biochem. & Biophys. Res. Comm., 2001; 288:156-64.

Azizi, S.A. et al., "Engraftment and Migration of Human Bone Marrow Stromal Cells Implanted in the Brains of Albino Rats—Similarities to Astrocyte Grafts," Proc. Natl. Acad. Sci. USA, 1998; 95:3908-13.

Bai, M., et al, "Dimerization of the Extracellular Calcium-sensing Receptor (CaR) on the Cell Surface of CaR-Transfected HEK293 Cells," J. Biol Chem., 1998; 273(36): 23605-23610.

Baker, K.A. et al., "Intrastriatal and Intranigral Grafting of hNT Neurons in the 6-OHDA Rat Model of Parkinson's Disease," Exper. Neurol., 2000; 162:350-60.

Balis, F. et al., "Central Nervous System Pharmacology of Antileukemic Drugs," Am. J. of Pediatric Hematol. Oncol., 1989; 11(1):74-86.

Balkema, G.W. et al., "Impaired Visual Thresholds in Hypopigmented Animals," Visual Neuroscience, 1991; 6:577-85.

Bao, Z.Z. et al., "Regulation of Chamber-Specific Gene Expression in the Developing Heart by IrX 4," Science, 1999; 283(5405):1161-64 (Abstract 1 page).

Barberi, T. et al., "Neural Subtype Specification of Fertilization and Nuclear Transfer Embryonic Stem Cells and Application in Parkinsonian Mice," Nature Biotechnology, 2003; 21(10):1200-07.

Beck, R.W. et al., "A Clinical Comparison of Visual Field Testing With a New Automated Perimeter, The Humphrey Field Analyzer, and The Goldmann Perimeter," Ophthalmology, 1985; 92(1):77-82.

Bergers, G. et al., "The Role of Pericytes in Blood-Vessel Formation and Maintenance," Neuro-Oncology, 2005; 7:452-64.

Bhindi, R. et al., "Rat Models of Myocardial Infarction," Thromb Haemost, 2006; 96:602-10.

Björklund, L.M. et al., "Embryonic Stem Cells Develop Into Functional Dopaminergic Neurons After Transplantation in a Parkinson Rat Model," PNAS, 2002; 99(4):2344-49.

Blakemore et al., "Modelling Large Areas of Demyelination in the Rat Reveals the Potential and Possible Limitations of Transplanted Glial Cells for Remyelination in the CNS," GLIA, 2002; 38:155-68.

Brodsky, S.V., "Coagulation, Fibrinolysis and Angiogenesis: New Insights From Knockout Mice," Exp. Nephrol., 2002; 10:299-306.

Brooks, P., "Inflammation as an Important Feature of Osteoarthritis," Bull. World Health Org., 2003; 81(9):689-90.

Brown, J.A. et al., "Blockade of Programmed Death-1 Ligands on Dendritic Cells Enhances T Cell Activation and Cytokine Production," J. Immunology, 2003; 170:1257-1266.

Burnstein, R.M. et al., "Differentiation and Migration of Long Term Expanded Human Neural Progenitors in a Partial Lesion Model of Parkinson's Disease," Intern. J. of Biochem. & Cell Biology, 2004; 36:702-13.

Caballero, S. et al., "The Many Possible Roles of Stem Cells in Age-Related Macular Degeneration," Graefe's Arch. Clin. Exp. Ophthalmol., 2004; 242:85-90.

Campbell, I.K. et al., "Human Articular Cartilage and Chondrocytes Produce Hemopoietic Colony-Stimulating Factors in Culture in Response to IL-1," J. of Immun., 1991; 147(4):1238-46.

Cao, Q. et al., "Stem Cell Repair of Central Nervous System Injury," J. of Neuroscience Res., 2002; 68:501-10.

Caplan, A.I. et al., "Mesenchymal Stem Cells: Building Blocks for Molecular Medicine in the 21st Century," Trends in Molecular Med., 2001; 7(6):259-64.

Carter, D. et al., "Characterization of MSC Potential to Treat GVHD Using Molecular Markers Linked to MSC-Mediated Immunosuppression in Vitro," Blood, 2005; 106(11) part 2, Abstract No. 4322, 160B.

"Cell Lysis, p. 2" http://www.piercenet.com/objects/view.cfm?type=Page&ID=1904ED25-8FA4-475C-8068-C2EB13D5F4E7; assessed Aug. 7, 2008.

Chagraoui, J. et al., "Fetal Liver Stroma Consists of Cells in Epithelial-To-Mesenchymal Transition," Blood, 2003; 101(8):2973-2982.

Chen, D., et al. "Differential Roles for Bone Morphogenic Protein (BMP) Receptor Type IB and IA in Differentiation and Specification of Mesenchymal Precursor Cells to Osteoblast and Adipocyte Lineages," J. Cell Biol., 1998; 142(1):295-305.

Cheng, A., et al. "Nitric Oxide Acts in a Positive Feedback Loop With BDNF to Regulate Neural Progenitor Cell Proliferation and Differentiation in the Mammalian Brain," Dev. Biol., 2003; 258:319-333.

Constantini, S. et al., "The Effects of Methylprednisolone and the Ganglioside GM1 on Acute Spinal Cord Injury in Rats," J. Neurosurg., 1994; 80(1):97-111.

Coumans, B. et al., "Lymphoid Cell Apoptosis Induced by Trophoblastic Cells: A Model of Active Foeto-Placental Tolerance," J. of Immunological Methods, 1999; 224:185-196.

D'Cruz, P.M. et al., "Mutation of the Receptor Tyrosine Kinase Gene Mertk in the Retinal Dystrophic RCS Rat," Hum. Mol. Genet., 2000; 9(4):645-651.

Daley, G.Q. et al., "Realistic Prospects for Stem Cell Therapeutics," Hematol., 2003; 398-418.

Danon, D. et al., "Macrophage Treatment of Pressure Sores in Paraplegia," J. Wound Care, 1998; 7(6):281-83.

Danon, D. et al., "Treatment of Human Ulcers by Application of Macrophages Prepared From a Blood Unit," Exp. Gerontol, 1997; 32(6):633-41.

Dawson, T.M. et al., "Neuroprotective and Neurorestorative Strategies for Parkinson's Disease," Nat. Neurosci., 2002; 5 Suppl.:1058-61.

Dimri, G.P. et al., "A Biomarker That Identifies Senescent Human Cells in Culture and in Aging Skin In Vivo," Proc. Natl. Acad. Sci. USA, 1995; 92:9363-67.

Domb, A. et al., "Degradable Polymers for Site-Specific Drug Delivery," Polymers for Advanced Technologies, 1992; 3:279-92.

Doshi, S.N. et al., "Evolving Role of Tissue Factor and Its Pathway Inhibitor," Critical Care Med., 2002; 30(5):S241-50.

Doyle, J., "Spiraling Complexity, Robustness, and Fragility in Biology," http://www.cds.caltech.edu/~doyle/CmplxNets/Bio1.pdf, available online Feb. 28, 2004.

Eagle, H., "The Specific Amino Acid Requirements of a Mammalian Cell (Strain L) in Tissue Culture," J. Biol. Chem., 1955; 214(2):839-52.

Eblenkamp, M. et al., "Umbilical Cord Stromal Cells (UCSC). Cells Featuring Osteogenic Differentiation Potential," Der Orthopade, Dec. 2004; 33:1338-45 (English abstract on p. 1339).

Edelstein, M. L. et al., "Gene Therapy Clinical Trials Worldwide 1989-2004—An Overview," J. Gene Med., 2004; 6(6):597-602.

Edlund, H., "Pancreatic Organogenesis—Developmental Mechanisms and Implications for Therapy," *Nat. Rev. Genet.*, 2002; 3:524-32.
Efrat, S. et al., "Cell Replacement Therapy for Type 1 Diabetes," *Trends in Molecular Medicine*, 2002; 8(7):334-39.
Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-74.
Ehtesham, M. et al., "The Use of Interleukin 12-Secreting Neural Stem Cells for the Treatment of Intracranial Glioma," *Cancer Res.*, 2002; 5657-63.
Eisenhofer, G.E. et al., "Tyrosinase: A Developmentally Specific Major Determinant of Peripheral Dopamine," *FASEB J.*, 2003; 17:1248-55.
Ende, N. et al., "Parkinson's Disease Mice and Human Umbilical Cord Blood," *J. Med.*, 2002; 33(1-4):173-80.
Engstad, C.S. et al., "The Effect of Soluble β-1,3-Glucan and Lipopolysaccharide on Cytokine Production and Coagulation Activation in Whole Blood," *Int. Immunopharmacol*, 2002; 2:1585-1597.
Enzmann, V. et al., "Enhanced Induction of RPE Lineage Markers in Pluripotent Neural Stem Cells Engrafted Into the Adult Rat Subretinal Space," *Investig. Ophthalmol. Visual Sci.*, 2003; 44(12):5417-22.
Erices et al., "Mesenchymal Progenitor Cells in Human Umbilical Cord Blood," Br. J. Haematol., 2000; 109(1):235-242.
Fazleabas, A.T. et al., "Endometrial Function: Cell Specific Changes in the Uterine Environment," *Mol. & Cellular. Endo.*, 2002; 186:143-147.
Fiegel, H.C. et al., "Liver-Specific Gene Expression in Cultured Human Hematopoietic Stem Cells," Stem Cells, 2003;21:98-104.
Foley, A. et al., "Heart Induction: Embryology to Cardiomyocyte Regeneration," *Trends Cardiovasc. Med.*, 2004; 14(3):121-25.
Franc, S. et al., "Microfibrillar Composition of Umbilical Cord Matrix : Characterization of Fibrillin, Collagen VI and Intact Collagen V," *Placenta*, 1988; 19:95-104.
Freed, C.R. et al., "Transplantation of Embryonic Dopamine Neurons for Severe Parkinson's Disease," *N. Engl. J. Med.*, 2001; 344(10):710-19.
Frenkel, O. et al., "Activated Macrophages for Treating Skin Ulceration: Gene Expression in Human Monocytes After Hypo-Osmotic Shock," *Clin. Exp. Immunol.*, 2002; 128:59-66.
Friedman, J.A. et al., "Biodegradable Polymer Grafts for Surgical Repair of the Injured Spinal Cord," *Neurosurgery*, 2002; 51(3):742-51.
Fukuchi, Y. et al., "Human Placenta-Derived Cells Have Mesenchymal Stem/Progenitor Cell Potential," *Stem Cells*, 2004; 22(5):649-58.
Fukuda, K., "Reprogramming of Bone Marrow Mesenchymal Stem Cells Into Cardiomyocytes," *C.R. Biol.*, 2002; 325:1027-1038.
Garbuzova-Davis et al., "Intravenous Administration of Human Umbilical Cord Blood Cells in a Mouse Model of Amyotrophic Lateral Sclerosis: Distribution, Migration, and Differentiation," Journal of Hematotherapy & Stem Cell Research, 2003; 12:255-270.
Gellersen, B. et al., "Cyclic AMP and Progesterone Receptor Cross-Talk in Human Endometrium: A Decidualizing Affair," *J. Endocrinol.*, 2003; 178(3):357-372.
Gerdes, D. et al., "Cloning and Tissue Expression of Two Putative Steroid Membrane Receptors," *Biol. Chem.*, 1998; 379:907-911.
Gökhan, S. et al., "Basic and Clinical Neuroscience Applications of Embryonic Stem Cells," *Anat. Rec. (New Anat)*, 2001; 265:142-56.
Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001: 7;581-588.
Gosiewska, A. et al., "Development of a Three-Dimensional Transmigration Assay for Testing Cell-Polymer Interactions for Tissue Engineering Applications," Tissue Eng., 2001; 7(3):267-277.
Gottleib, D.I. "Large-Scale Sources of Neural Stem Cells," *Annu. Rev. Neurosci.*, 2002; 25:381-407.
Gupta, S. et al., "Isolation and Characterization of Kidney-Derived Stem Cells," *J. of Am. Soci. of Nephrol.*, 2006; 17(11):3028-40.

Halvorsen, Y.C. et al., "Extracellular Matrix Mineralization and Osteoblast Gene Expression by Human Adipose Tissue-Derived Stromal Cells," *Tissue Eng.*, 2001; 7(6):729-741.
Hanahan, D. "Heritable Formation of Pancreatic β-Cell Tumours in Transgenic Mice Expressing Recombinant Insulin/Simian Virus 40 Oncogenes," *Nature*, 1985; 315:115-122.
Haruta, M. et al., "In Vitro and in Vivo Characterization of Pigment Epithelial Cells Differentiated From Primate Embryonic Stem Cells," *Investig. Ophthalmol. & Visual Sci.*, 2004; 45(3):1020-25.
Hayflick, L., "The Longevity of Cultured Human Cells," *J. Am. Geriatr. Soc.*, 1974; 22(1):1-12.
Hayflick, L., "The Strategy of Senescence," *Gerontologist*, 1974; 14(1):37-45.
Hongpaisan, J., "Inhibition of Proliferation of Contaminating Fibroblasts by D-Valine in Cultures of Smooth Muscle Cells From Human Myometrium," *Cell Biol. Int.*, 2000; 24(1):1-7.
Hoynowski, S.M. et al., "Characterization and Differentiation of Equine Umbilical Cord-Derived Matrix Cells," *Biochemical and Biophysical Research Communications*, 2007; 362:347-53.
Hu, A. et al., "Hepatic Differentiation From Embryonic Stem Cells in Vitro," *Chin. Med. J.*, 2003; 116(12):1893-97.
Isacson, O., "The Production and Use of Cells As Therapeutic Agents in Neurodegenerative Diseases," *The Lancet (Neurology)*, 2003; 2:417-424.
Isacson, O., et al., "Specific Axon Guidance Factors Persist in the Adult Brain as Demonstrated by Pig Neuroblasts Transplanted to the Rat," *Neurosci.*, 1996; 75(3):827-37.
Ishii, M. et al., "Molecular Markers Distinguish Bone Marrow Mesenchymal Stem Cells From Fibroblasts," *Biochemical and Biophysical Research Communications*, Jun. 24, 2005; 332(1):297-303.
Ito, Y. et al., "A Quantitative Assay Using Basement Membrane Extracts to Study Tumor Angiogenesis In Vivo," *Int. J. Cancer*, 1996; 67:148-152.
Jackson, K.A. et al., "Regeneration of Ischemic Cardiac Muscle and Vascular Endothelium by Adult Stem Cells," *J. Clin. Invest.*, 2001; 107:1395-1402.
Jaffe, E.A. et al., "Culture of Human Endothelial Cells Derived From Umbilical Veins; Identification by Morphologic and Immunologic Criteria" *J Clin Invest*, 1973; 52:2745-56.
Jaiswal et al., Adult Human Mesenchymal Stem Cell Differentiation to the Osteogenic or Adipogenic Lineage is Regulated by Motogen-Activated Protein Kinase, J. Biol. Chem., 2000; 275(13):9645-9652.
Janderová, L. et al., "Human Mesenchymal Stem Cells as an in Vitro Model for Human Adipogenesis," *Obes. Res.*, 2003; 11(1):65-74.
Jang, Y.K. et al., "Retinoic Acid-Mediated Induction of Neurons and Glial Cells From Human Umbilical Cord-Derived Hematopoietic Stem Cells," *J. Neurosci. Res.*, 2004; 75:573-584.
Jikuhara, T. et al., "Left Atrial Function As a Reliable Predictor of Exercise Capacity in Patients With Recent Myocardial Infarction," *Chest*, 1997; 111(4):922-28.
Johe, K.K. et al., "Single Factors Direct the Differentiation of Stem Cells From the Fetal and Adult Central Nervous System," *Genes & Devel.*, 1996;10:3129-40.
Johnstone, B. et al., "In Vitro Chondrogenesis of Bone-Marrow-Derived Mesenchymal Progenitor Cells," *Exp. Cell Res.*, 1998; 238:265-272.
Jomura, S. et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.
Jones, J. et al., "Insulin-Like Growth Factors and their Binding Proteins: Biological Actions," *Endocrine Review*, 1995; 16(1):3-34.
Jones-Villeneuve, E.M. et al., "Retinoic Acid-Induced Neural Differentiation of Embryonal Carcinoma Cells," *Mol. & Cellu. Biol.*, 1983; 3(12):2271-2279.
Joussen, A.M. "Cell Transplantation in Age Related Macular Degeneration: Current Concepts and Future Hopes," *Graefe's Arch. Clin. Exp. Ophthalmol.*, 2004; 242:1-2.
Kadiyala, S. et al., "Culture Expanded Canine Mesenchymal Stem Cells Possess Osteochondrogenic Potential in Vivo and in Vitro," *Cell Transplant.*, 1997; 6(2):125-134.
Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.*, Sep. 1984; 160:633-51.

Kicic, A. et al., "Differentiation of Marrow Stromal Cells Into Photoreceptors in the Rat Eye," *J. of Neurosci.*, 2003; 23(21):7742-49.

Kim, J. et al., "Dopamine Neurons Derived From Embryonic Stem Cells Function in an Animal Model of Parkinson's Disease," *Nature*, 2002; 418:50-56.

Kim, J.Y. et al., "Ocular Surface Reconstruction: Limbal Stem Cell Transplantation," *Ophthal. Clin. N. Am.*, 2003; 16:67-77.

Kim, S.K. et al., "Intercellular Signals Regulating Pancreas Development and Function," *Genes Dev.*, 2001; 15:111-27.

Kirschstein, R. et al., "Can Stem Cells Repair a Damaged Heart?" *Stem Cells: Scientific Progress and Future Research Directions*, 2001; 87-92.

Laface, D. et al., "Gene Transfer Into Hematopoietic Progenitor Cells Mediated by an Adeno-Associated Virus Vector," *Virology*, 1998; 162:483-86.

Lang, K.J.D. et al., "Differentiation of Embryonic Stem Cells to a Neural Fate: A Route to Re-Building the Nervous System?" *J. of Neurosci. Res.*, 2004; 76:184-92.

Langeggen, H. et al., "HUVEC Take Up Opsonized Zymosan Particles and Secrete Cytokines IL-6 and IL-8 in Vitro," *FEMS Immunol. Med. Microbiol.*, 2003; 36:55-61.

Le Belle, J.E. et al., "Stem Cells for Neurodegenerative Disorders: Where Can We Go From Here?," Biodrugs, 2002; 16(6):389-401.

Le Bouteiller, P. et al., "Soluble HLA-G1 At the Materno-Foetal Interface—A Review," *Placenta*, 2003; 24 (Suppl. A):S10-S15.

Li, A. et al., "IL-8 Directly Enhanced Endothelial Cell Survival, Proliferation, and Matrix Metalloproteinases Production and Regulated Angiogenesis," *J. Immunol.*, 2003; 170(6):3369-3376.

Li, Y. et al., "Transplanted Olfactory Ensheathing Cells Promote Regeneration of Cut Adult at Optic Nerve Axons," *J. of Neuro.*, 2003; 23(21):7783-7788.

Li, Y. et al., "Intracerebral Transplantation of Bone Marrow Stromal Cells in A 1-Methyl-4-Phenyl-1,2,3,6-Tetrahydropyridine Mouse Model of Parkinson's Disease," *Neuroscience Letts.*, 2001; 315:67-70.

Lian, et al., "Human Umbilical Cord Wharton's Jelly-Derived Mesenchymal Stem Cells Differentiation into Nerve-Like Cells," Chinese Medical Journal, 2005; 118(23):1, pp. 1987-1993.

Liddiard, et al., "An Improved Method for the Preparation of Human Fetal and Adult Hepatocytes," Arch. Toxicol., 1980; 44(1-3):107-112.

Lindenlaub, T. et al., "Partial Sciatic Nerve Transection as a Model of Neuropathic Pain: A Qualitative and Quantitative Study," PAIN, 2000; 89(1): 97-106.

Lindvall, O. et al., "Stem Cell Therapy for Human Neurodegenerative Disorders—How to Make It Work," *Nature Medicine*, 2004;10(Suppl.):S42-S50.

Liu, Y. et al., "Molecular and Genetic Mechanisms of Obesity: Implications for Future Management," *Curr. Mol. Med.*, 2003; 3(A):325-340.

Lockhart, D.J. et al., "Expression Monitoring by Hybridization to High-Density Oligonucleotide Arrays," *Nat. Biotechnol.*, 1996;14(13):1675-80.

Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-51.

Lund, R.D. et al., "Cell Transplantation as a Treatment for Retinal Disease," *Progress in Retinal and Eye Research*, 2001; 20(4):416-449.

Lund, R.D. et al., "Subretinal Transplantation of Genetically Modified Human Cell Lines Attenuates Loss of Visual Function in Dystrophic Rats," *PNAS*, 2001; 98(17):9942-9997.

Lund, R.L. et al., "Retinal Transplantation: Progress and Problems in Clinical Application," *J. Leukocyte Biol.*, 2003; 74:151-60.

Luo, D. et al., "Synthetic DNA Delivery Systems," *Nat. Biotechnol.*, 2000; 18(1):33-36.

Luyten, F.P. et al., "Skeletal Tissue Engineering: Opportunities and Challenges," *Best Pract. Res. Clin. Rheumatol.*, 2001; 15(5):759-69.

Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.

MacDonald, R.J. "Expression of the Pancreatic Elastase I Gene in Transgenic Mice," *Hepatology*, 1987; 7(1):42S-51S.

MacKay, A.M. et al., "Chondrogenic Differentiation of Cultured Human Mesenchymal Stem Cells From Marrow," *Tissue Engineering*, 1998; 4(4):415-28.

Marx, W.F. et al., "Endovascular Treatment of Experimental Aneurysms by use of Biologically Modified Embolic Devices: Coil-Mediated Intraaneurysamal Delivery of Fibroblast Tissue Allografts," *Am. J. Neuroradiol.*, 2001; 22:323-33.

Mason, A.J. et al., "The Hypogonadal Mouse: Reproductive Functions Restored by Gene Therapy," *Science*, 1986; 234:1372-1378.

Mayer-Proschel, M. et al., "Isolation of Lineage-Restricted Neuronal Precursors From Multipotent Neuroepithelial Stem Cells," *Neuron.*, 1997; 19:773-785.

McDonald, J.A. et al., "Diminished Responsiveness of Male Homosexual Chronic Hepatitis B Virus Carriers With HTLV-III Antibodies to Recombinant α-Interferon," *Hepatology*, 1987; 7(4):719-23.

Medicetty, S. et al., "Transplantation of Human Umbilical Cord Matrix Stem Cells Alleviates Apomorphine-Induced Rotations in Parkinsonian Rats", 2003, XP-002383776, 1 page.

Melero-Martin, J. et al., "Optimal In-Vitro Expansion of Chondroprogenitor Cells in Monolayer Culture," *Biotechnology and Bioengineering*, 2006; 93(3):519-33.

Merx, M.W. et al., "Transplantation of Human Umbilical Vein Endothelial Cells Improves Left Ventricular Function in a Rat Model of Myocardial Infarction," *Basic Res. Cardiol.*, 2005; 100:208-16.

Messina, D.J., et al., "Comparison of Pure and Mixed Populations of Human Fetal-Derived Neural Progenitors Transplanted Into Intact Adult Rat Brain,"*Exper. Neurol.*, 2003; 184:816-829.

Mitchell, K.E. et al., "Matrix Cells From Wharton's Jelly Form Neurons and Glia," *Stem Cells*, 2003; 21:50-60.

Moll, S. et al., "Monitoring Warfarin Therapy in Patients With Lupus Anticoagulants," *Ann. Intern. Med.*, 1997; 127(3):177-85.

Mombaerts, P. et al., "Creation of a Large Genomic Deletion at the T-Cell Antigen Receptor β-Subunit Locus in Mouse Embryonic Stem Cells by Gene Targeting," *Proc. Nat. Acad. Sci. USA*, 1991; 88:3084-3087.

Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.*, 1990; 18(12):3587-96.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Moulder, J.E., "Pharmacological Intervention to Prevent or Ameliorate Chronic Radiation Injuries," *Semin. Radiat. Oncol.*, 2003; 13(1):73-84.

Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26(2):119-128.

Nishida, K. et al., "Functional Bioengineered Corneal Epithelial Sheet Grafts From Corneal Stem Cells Expanded Ex Vivo on a Temperature-Responsive Cell Culture Surface," *Transplantation*, 2004; 77(3):379-85.

Nishishita, T. et al., "A Potential Pro-Angiogenic Cell Therapy With Human Placenta-Derived Mesenchymal Cells," *Biochemical and Biophysical Research Communications*, 2004; 325:24-31.

Nixon, P.J. et al., "The Contribution of Cone Responses to Rat Electroretinograms," *Clin. Experiment Ophthalmol.*, 2001; 29(3):193-196.

Nork, T.M. et al., "Swelling and Loss of Photoreceptors in Chronic Human and Experimental Glaucomas," *Arch. Ophthalmol.*, 2000; 118:235-45.

Oh, S.H. et al., "Hepatocyte Growth Factor Induces Differentiation of Adult Rat Bone Marrow Cells Into a Hepatocyte Lineage in Vitro," *Biochem. & Biophys. Res. Comm.*, 2000; 279(2):500-04.

Okumoto, K. et al., "Differentiation of Bone Marrow Cells Into Cells That Express Liver-Specific Genes in Vitro: Implication of the Notch Signals in Differentiation," *Biochem. & Biophys. Res. Commun.*, 2003; 304:691-695.

Orlic, D. et al., "Stem Cells for Myocardial Regeneration," *Circ. Res.*, 2002; 91:1092-1102.

Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.

Osborne, N.N. et al., "Some Current Ideas on the Pathogenesis and the Role of Neuroprotection in Glaucomatous Optic Neuropathy," *Eur. J. Ophthalmol.*, 2003; 13(Supp. 3):S19-S26.

Palu, G. et al., "In Pursuit of New Developments for Gene Therapy of Human Diseases," *J. Biotechnol.*, Feb. 1999; 68(1):1-13.

Pittenger, M.F. et al., "Multilineage Potential of Adult Human Mesenchymal Stem Cells," *Science*, 1999; 284:143-47 and seven pages of online supplementary material.

Pittenger, M.F. et al., "Mesenchymal Stem Cells and Their Potential as Cardiac Therapeutics," *Circ. Res.*, 2004; 95:9-20.

Plaia, T., et al., "Characterization of a New Nih-Registered Variant Human Embryonic Stem Cell Line, BG01V: A Tool for Human Embryonic Stem Cell Research," *Stem Cells*, 2006: 24(3): 531-546.

Pountos, I. et al., "Mesenchymal Stem Cell Tissue Engineering: Techniques for Isolation, Expansion and Application," *Injury*, 2007; 38(Supp. 4):S23-33.

Rabbany, S.Y. et al., "Molecular Pathways Regulating Mobilization of Marrow-Derived Stem Cells for Tissue Revascularization," *Trends in Molecular Med.*, 2003; 9(3):109-17.

Rafii, S. et al., "Therapeutic Stem and Progenitor Cell Transplantation for Organ Vascularization and Regeneration," *Nature Med.*, 2003; 9(6):702-12.

Ratner, B.D., et al., "Biomaterials: Where We Have Been and Where we are Going," Annu. Rev. Biomed. Eng., 2004; 6:41-75.

Readhead, C. et al., "Expression of a Myelin Basic Protein Gene in Transgenic Shiverer Mice: Correction of the Dysmyelinating Phenotype," *Cell*, 1987; 48(4):703-712.

Refaie, A. et al., "Experimental Islet Cell Transplantation in Rats: Optimization of the Transplantation Site," *Trans. Proc.*, 1998; 30:400-403.

Rehman, J. et al., "Secretion of Angiogenic and Antiapoptotic Factors by Human Adipose Stromal Cells," *Circulation*, 2004; 109:1292-98.

Reubinoff, B.E. et al., "Neural Progenitors From Human Embryonic Stem Cells," *Nature Biotechnology*, 2001; 19:1134-40.

Reyes, M. et al., "Purification and Ex Vivo Expansion of Postnatal Human Marrow Mesodermal Progenitor Cells," *Blood*, 2001; 98(9):2615-25.

Rezai, K.A. et al., "Iris Pigment Epithelium Transplantation," *Graefe's Arch. Clin. Ophthalmol.*, 1997; 235:558-62.

Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.

Rios, M. et al., "Catecholamine Synthesis is Mediated by Tyrosinase in the Absence of Tyrosine Hydroxylase," *J. Neurosci.*, 1999, 19(9): 3519-26.

Romanov, Y.A. et al., "Searching for Alternative Sources of Postnatal Human Mesenchymal Stem Cells," *Stem Cells*, 2003; 21:105-10.

Rosen, E.M. et al., "HGF/SF in Angiogenesis," *Ciba Found. Symp.*, 1997; 212:215-229.

Roskams, A.J. et al., "Directing Stem Cells and Progenitor Cells on the Stage of Spinal Cord Injury," *Exp. Neurol.*, 2005; 193:267-72.

Rutherford, A. et al., "Eyeing-Up Stem Cell Transplantation," *Trends in Molecular Medicine*, 2003; 7(1):11.

Sagrinati, C. et al., "Isolation and Characterization of Multipotent Progenitor Cells from the Bowman's Capsule of Adult Human Kidney," *Journal of American Society of Nephrology*, 2006; 17(9)2443-56.

Sahn, D.J. et al., "Recommendations Regarding Quantitation in M-Mode Echocardiography: Results of a Survey of Echocardiographic Measurements," *Circulation*, 1978; 58(6):1072-83.

Sakariassen, K.S. et al., "Methods and Models to Evaluate Shear-Dependent and Surface Reactivity-Dependent Antithrombotic Efficacy," *Thromb. Res.*, 2001; 104:149-174.

Salcedo, R. et al., "Human Endothelial Cells Express CCR2 and Respond to MCP-1: Direct Role of MCP-1 in Angiogenesis and Tumor Progression," *Blood*, 2000; 96(1):34-40.

Salgado, A.J. et al., "Bone Tissue Engineering: State of the Art and Future Trends," *Macromol. Biosci.*, Aug. 2004; 4:743-65.

Schouten, J.W. et al., "A Review and Rationale for the Use of Cellular Transplantation as a Therapeutic Strategy for Traumatic Brain Injury," *Journal of Neurotrauma*, 2004; 21(11):1501-38.

Schraermeyer, U. et al., "Subretinally Transplanted Embryonic Stem Cells Rescue Photoreceptor Cells From Degeneration in the RCS Rats," *Cell Transplantation*, 2001; 10:673-80.

Schreuder, G.M. et al., "The HLA Dictionary 1999: A Summary of HLA-A, -B, -C,-DRB1/3/4/5, -DQB1 Alleles and Their Association with Serologically Defined HLA-A, -B, -C, -DR and -DQ Antigens," *Tissue Antigen*, 1999; 54(4):409-37.

Schwartz, R.E. et al., "Multipotent Adult Progenitor Cells From Bone Marrow Differentiate Into Functional Hepatocyte-Like Cells," *J. of Clin. Invest.*, 2002; 109(10):1291-1302.

Sebire, G. et al., "In Vitro Production of IL-6,IL-1 β, and Tumor Necrosis Factor-α by Human Embryonic Microglial and Neural Cells," *J. Immunol.*, 1993; 150(4):1517-23.

Sethe, S. et al., "Aging of Mesenchymal Stem Cells," *Ageing Research Reviews*, 2006; 5:91-116.

Shani, M., "Tissue-Specific Expression of Rat Myosin Light-Chain 2 Gene in Transgenic Mice," *Nature*, 1985; 314(6008):283-286.

Shimizu, T. et al., "Cell Sheet Engineering for Myocardial Tissue Reconstruction," *Biomaterials*, 2003; 24:2309-2316.

Siminoff, R. et al., "Properties of Reptilian Cutaneous Mechanoreceptors," *Exp. Neurol.*, 1968; 20(3):403-14.

Sommer, et al., "Ocular Tissue Engineering," Ad. Exptl. Med. Biol., 2007, 585, pp. 413-429.

Song, H. et al., "Astroglia Induce Neurogenesis From Adult Neural Stem Cells," *Nature*, 2002; 417(6884):39-44.

Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12:355-364.

Storch, T.G. "Oxygen Concentration Regulates 5-Azacytidine-Induced Myogenesis in $C_3H/10T1/2$ cultures," *Biochim. Biophys. Acta*, 1990; 1055:126-129.

Street, C.N. et al., "Stem Cells: A Promising Source of Pancreatic Islets for Transplantation in Type 1 Diabetes," *Curr Top Dev. Biol.*, 2003; 58:111-36.

Svendsen, C.N. et al., "Long-Term Survival of Human Central Nervous System Progenitor Cells Transplanted Into a Rat Model of Parkinson's Disease," *Experim. Neural.*, 1997; 148:135-46.

Swift, G.H. et al., "Tissue-Specific Expression of the Rat Pancreatic Elastase I Gene in Transgenic Mice," *Cell*, 1984; 38:639-646.

Taylor, D.A. et al., "Regenerating Functional Myocardium: Improved Performance After Skeletal Myoblast Transplantation," *Nature Medicine*, Aug. 1998; 4(8):929-33 (Erratum in *Nature Medicine*, 1998; 4(10):1200).

Taylor, D.A. et al., "Cardiac Chimerism as a Mechanism for Self-Repair: Does It Happen and if so to What Degree?" *Circulation*, 2002; 106(1):2-4.

Toma, C. et al., "Human Mesenchymal Stem Cells Differentiate to a Cardiomyocyte Phenotype in the Adult Murine Heart," Circulation 2002; 105:93-98.

Tomita, M. et al., "Bone Marrow-Derived Stem Cells Can Differentiate Into Retinal Cells in Injured Rat Retina," *Stem Cells*, 2002; 20:279-83.

Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001; 19:408-18.

Tresco, P.A. et al., "Cellular Transplants As Sources for Therapeutic Agents," *Advanced Drug Delivery Reviews*, 2000; 42:3-27.

Turner, J.F., "Inherited Retinal Dystrophy in the RCS Rat: Prevention of Photoreceptor Degeneration by Pigment Epithelial Cell Transplantation," *Exp. Eye Res.*, 1988; 47:911-17.

Tusher, V.G. et al., "Significance Analysis of Microarrays Applied to the Ionizing Radiation Response," *PNAS*, 2001; 98(9):5116-5121.

Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.

Ulloa-Montoya, F. et al., "Culture Systems for Pluripotent Stem Cells," *Journal of Bioscience and Bioengineering*, 2005; 100(1):12-27.

Urbich, C. et al., "Endothelial Progenitor Cells Characterization and Role in Vascular Biology,", *Circ. Res.*, 2004; 95:343-53.

Van Hoffelen, S.J. et al., "Incorporation of Murine Brain Progenitor Cells Into the Developing Mammalian Retina," *Invest. Ophthalmol. Vis. Sci.*, 2003; 44(1):426-34.

Vassliopoulos, G. et al., "Transplanted Bone Marrow Regenerates Liver by Cell Fusion," *Nature*, 2003(6934); 422:901-04.

Vermot-Desroches, C. et al., "Heterogeneity of Antigen Expression Among Human Umbilical Cord Vascular Endothelial Cells: Identification of Cell Subsets by Co-Expression of Haemopoietic Antigens," *Immunol. Lett.*, 1995; 48:1-9.

von Koskull, H. et al., "Induction of Cytokeratin Expression in Human Mesenchymal Cells," *J. Cell Physiol.*, 1987; 133:321-29.

Walboomers, X .F. et al., "Cell and Tissue Behavior on Micro-Grooved Surfaces," *Odontology*, 2001; 89:2-11.

Wang, X . et al., "Cell Fusion Is the Principal Source of Bone-Marrow-Derived Hepatocytes," *Nature*, 2003; 422(6934):897-900.

Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-92.

Woodbury, D., et al., "Adult Rat and Human Bone Marrow Stromal Cells Differentiate Into Neurons," *J. Neurosci. Res.*, 2000; 61(4):364-370.

Wulf, G.G. et al., "Mesengenic Progenitor Cells Derived From Human Placenta," *Tissue Engineering*, Larchmont, NY, Jul. 2004; 10(7/8):1136-47.

Xu, C. et al., "Characterization and Enrichment of Cardiomyocytes Derived From Human Embryonic Stem Cells," *Circ. Res.*, 2002; 91(5):501-508.

Xu, Y. et al., "Dopamine, in the Presence of Tyrosinase, Covalently Modifies and Inactivates Tyrosine Hydroxylase," *J. Neurosci. Res.*, 1998; 54(5):691-97.

Yang, C. et al., "Enhancement of Neovascularization With Cord Blood CD133[+] Cell-Derived Endothelial Progenitor Cell Transplantation," *Thrombosis and Haemostasis*, Jun. 2004; 91(6):1202-12.

Yang, H. et al., "Region-Specific Differentiation of Neural Tube-Derived Neuronal Restricted Progenitor Cells After Heterotopic Transplantation," *PNAS*, 2000; 97(24):13366-71.

Ye Q. et al., "Recovery of Placental-Derived Adherent Cells With Mesenchymal Stem Cell Characteristics", *Blood*, 2001; 98(11 Part 2):147B (Abstract No. 4260).

Yip, H.K. and So, K.F., "Axonal Regeneration of Retinal Ganglion Cells: Effect of Trophic Factors," *Prog. Retin Eye Res.*, 2000; 19(5):559-575.

Yokoo, T. et al., "Stem Cell Gene Therapy for Chronic Renal Failure," *Curr Gene Ther.*, 2003; 3:387-94.

Yu, M. et al., "Mid-Trimester Fetal Blood-Derived Adherent Cells Share Characteristics Similar to Mesenchymal Stem Cells But Full-Term Umbilical Cord Blood Does Not," *British J. Haematology*, 2004; 124:666-75.

Zangani, D. et al., "Multiple Differentiation Pathways of Rat Mammary Stromal Cells in Vitro: Acquisition of a Fibroblast, Adipocyte or Endothelial Phenotype Is Dependent on Hormonal and Extracellular Matrix Stimulation," *Differentiation*, 1999; 64(2):91-101.

Zeng, B.Y. et al., "Regenerative and Other Responses to Injury in the Retinal Stump of the Optic Nerve in Adult Albino Rats: Transection of the Intracranial Optic Nerve," *J. Anat.*, 1995; 186:495-508.

Zhang, S. et al., "In Vitro Differentiation of Transplantable Neural Precursors From Human Embryonic Stem Cells," *Nature Biotechnology*, 2001; 19:1129-33.

Zhang, Y. et al., "Comparison of Mesenchymal Stem Cells from Human Placenta and Bone Marrow," *Chinese Medical Journal*, 2004; 117(6):882-87.

Zimmerman, S. et al., "Lack of Telomerase Activity in Human Mesenchymal Stem Cells," *Leukemia*, 2003; 17:1146-49.

* cited by examiner

METHODS FOR STERILIZING MATERIALS CONTAINING BIOLOGICALLY ACTIVE AGENTS

CROSS-REFERENCE TO RELATED APPLICATIONS

This application claims benefit to U.S. Provisional Patent Application No. 61/015,350, filed Dec. 20, 2007, the contents of which are incorporated by reference herein, in their entirety.

FIELD OF THE INVENTION

The present application pertains to sterilized biologically-active materials and methods for producing same.

BACKGROUND OF THE INVENTION

The commercial production of therapeutic clinical products containing biological derivatives requires sterilization methods to effectively eliminate bio-burden.

Expanded Human Umbilical Tissue Derived Cells (hUTC) are being developed as a potential cell therapy for the treatment of various degenerative diseases. In addition, cell derivatives (such as trophic factors, proteins, and other molecules) are also being developed as potential therapeutic agents. These derivatives can be used alone or in combination with biomaterials to augment cellular response. Upon deployment directly or indirectly to a target injury site, the derivatives may reduce excessive inflammation, reduce apoptosis and necrosis of endogenous cells of the injury site, induce differentiation of endogenous progenitor cells, increase neovascularization and angiogenesis, and promote new tissue formation. Alone, the derivatives can be deployed as a lyophilized powder, or combined with an aqueous or viscous delivery vehicle. The derivatives can also be combined with and released from biomaterials. For example, the application of the hUTC lysate to biomaterials followed by lyophilization produces a device applicable to tissue engineering and regenerative medicine. Additional information may be found in WO 2005/003334 (filed as PCT/US2004/020931, Jun. 25, 2004), and WO/2006/071794 (filed as PCT/US2005/046851, Dec. 22, 2005), both of which are incorporated herein by reference in their entireties.

However, current methods of sterilization of hUTC and other products containing biological derivatives, while being effective from the sterilization standpoint, reduce the biological activity of the derivatives. Previous approaches have made use of protective agents in combination with the biological sample. See, e.g., U.S. Pat. No. 5,730,933 (disclosing methods that comprise the step of forming a mixture of the biological sample with an extraneous protein, and optionally a free-radical scavenger, prior to irradiation). Such methods have the disadvantage of requiring additional processing steps and materials in addition to the sterilization protocol. Other previous methods perform sterilization in the presence of hydrogen gas. See U.S. 2004/0101958. Improved methods for sterilizing materials that contain active biological derivatives, as well as sterilized yet efficacious clinical products, are needed.

SUMMARY OF THE INVENTION

Provided are methods for sterilizing a material comprising a biologically-active agent comprising irradiating said material with ionizing radiation at a dose of about 5 kGy to about 25 kGy while maintaining said material in an atmosphere comprising at least 95% by volume inert gas and at a temperature of about 4° C. or lower.

Also provided are sterilized materials comprising a biologically-active agent, wherein said materials exhibit substantially the same amount of biological activity as a non-sterilized control.

DETAILED DESCRIPTION OF ILLUSTRATIVE EMBODIMENTS

Figure 1:
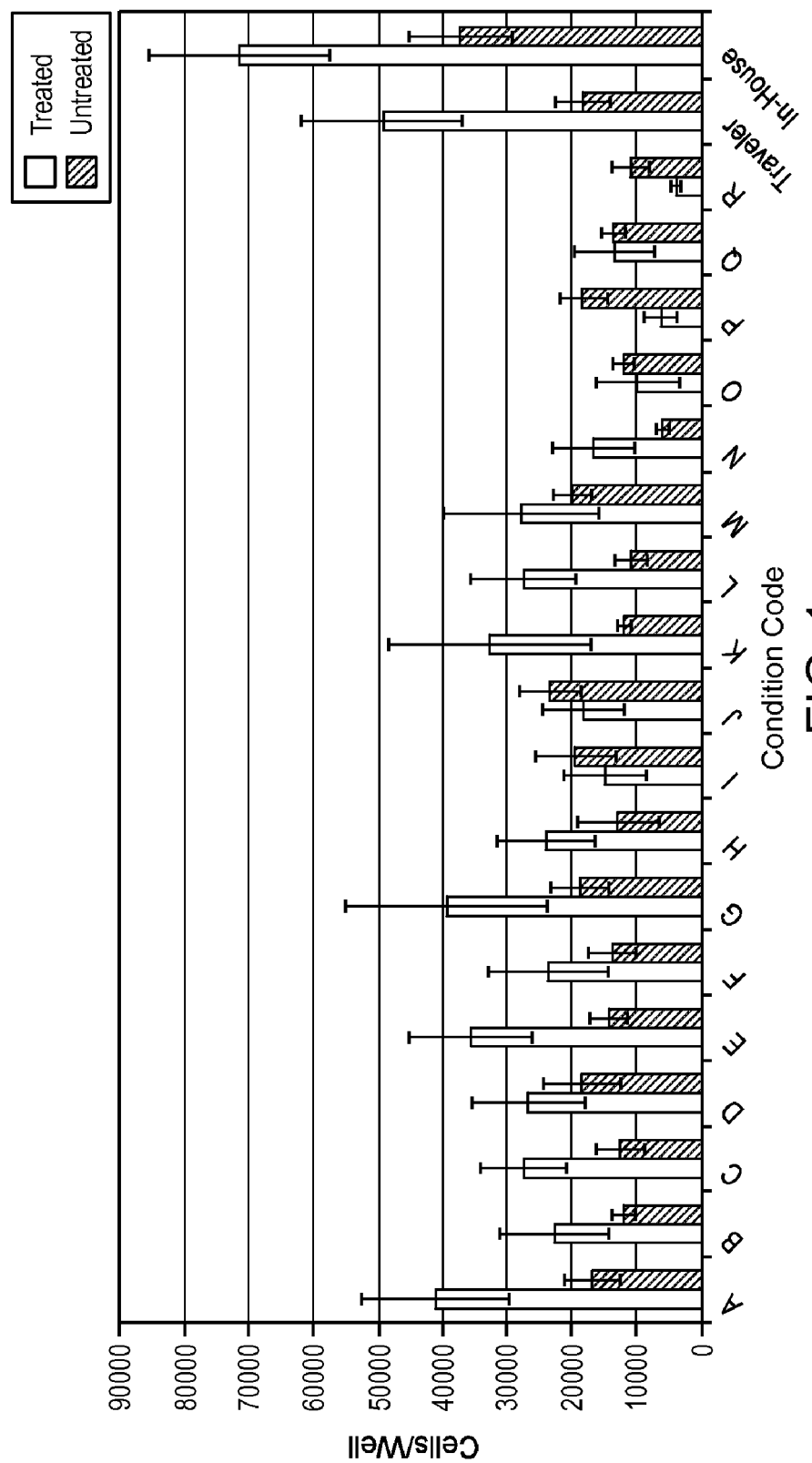
FIG. 1 depicts the measured average quantity of average cells per well of NIH/3T3 mouse fibroblasts co-cultured with gamma-irradiated collagen/ORC samples that are either treated with 150 μg hUTC lysate protein or left untreated.

Materials containing biologically-active agents must be subjected to sterilization prior to clinical use. However, this medically-necessary sterilization is traditionally accompanied by the attrition of the biological activity of the therapeutic ingredients, which leads to decreased clinical efficacy and necessitates the use of greater quantities of what are often costly materials.

Provided are methods for sterilizing a material comprising a biologically-active agent comprising irradiating said material with ionizing radiation at a dose of about 5 kGy to about 25 kGy while maintaining said material in an atmosphere comprising at least 95% by volume inert gas and at a temperature of about 4° C. or lower. The instant methods permit the retention of biological activity even while thorough sterilization is accomplished. The biological activity of samples according to the present invention is functionally comparable to that of non-sterilized controls, and the instant methods are therefore highly advantageous over previous methods that effectively represented a trade-off between sterilization and biological efficacy.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. Where present, all ranges are inclusive and combinable.

The biologically active agent may comprise cells, cell derivatives, growth factors, or any combination thereof. Exemplary cells for use in connection with the present invention include epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, melanocytes, dermal fibroblasts, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors such as CD34+ or CD34+/CD117+ cells), myoblasts, myocytes, hepatocytes, smooth muscle cells, striated muscle cells, stromal cells, other soft tissue cells or progenitor cells, chondrocytes, osteoblasts, islet cells, nerve cells, placenta-derived cells, human umbilical tissue derived cells, human kidney derived cells, or any combination thereof. Additional information regarding human kidney derived cells may be found in PCT/US2007/021708, filed Oct. 11, 2002, which is herein incorporated by reference in its entirety.

"Cell derivatives" include any material that is acquired from or made by a cell of any type, including, inter alia, organelles, membrane and membrane components, cytoskeletal elements, proteins, hormones, genetic material, and the like. In some embodiments, the biologically active agent is a cell derivative that comprises cell lysate, trophic factors, growth factors, cytokines, conditioned media, or any combination thereof. Exemplary growth factors are readily appreciated by those skilled in the art, e.g., PDGF-BB, bFGF, TGF-beta, HGF, VEGF, or GDF-5. Any biologically active component is considered to fall within the scope of the present invention. For example, expanded human umbilical tissue derived cells (hUTC), as well as cell lysate from hUTCs, are being developed as a potential therapy for the treatment of various degenerative diseases, and sterilization thereof in accordance with the present invention represents a considerable improvement upon such therapeutic protocols.

The material comprising a biologically active agent may further comprise a scaffold material. Thus, biologically active agents such as cells, cell derivatives, growth factors, and other molecules can be used alone or in combination with scaffolds, such as biomaterial scaffolds, to augment cellular response. For example, the application of the hUTC lysate to biomaterial scaffold followed by lyophilization produces a device applicable to tissue engineering and regenerative medicine: hUTC lysate combined with a collagen/oxidized regenerated cellulose (ORC) matrix or polyglactin 910 may be used in these and other contexts. The scaffold material may be naturally or synthetically derived. Exemplary scaffold materials include collagen, cellulose, fibrin, elastin, gelatin, demineralized bone, hyaluronic acid, poly(lactic acid), poly(glycolic acid), polycaprolactone, polyanhydrides, polyhydroxybutyrates, or any combination thereof. Those skilled in the art will readily appreciate other materials that may be used to provide the contemplated structural matrix in accordance with the present invention.

Irradiation of the material comprising a biologically active agent may be performed in accordance with traditional techniques, i.e., using any known sterilization medium or delivery mechanism. For example, the ionizing radiation may comprise, alpha radiation, beta radiation, gamma radiation, X-rays, electron beams, other subatomic particles, or any combination thereof. The dose of ionizing radiation is preferably about 5 kGy to about 25 kGy. In other embodiments, the dose of ionizing radiation is about 6 kGy to about 12 kGy. The dose of ionizing radiation may also be about 6 kGy to about 8 kGy, or may be about 7 kGy.

Pursuant to the present invention, the irradiation of the material comprising a biologically active agent occurs while maintaining the material in an atmosphere that is at least 95% by volume inert gas. The portion of the atmosphere comprising 95% by volume inert gas may comprise a single inert gas, or a combination of two or more inert gases. As used herein, "inert gas" refers to elemental as well as molecular gases that are not reactive under normal circumstances. Exemplary inert gases include noble gases, nitrogen, and other gases and gas mixtures as appreciated by those skilled in the art. The portion of the atmosphere comprising 95% by volume inert gas may comprise solely of nitrogen, and in other embodiments, the atmosphere may comprise about 100% by volume nitrogen.

One skilled in the art will readily appreciate various methods for providing a gaseous atmosphere in accordance with the present invention. The atmosphere in accordance with the present invention may be accomplished by containing the material comprising a biologically active agent in a sealed environment that is continuously flushed with the desired gaseous components, that has been pre-flushed one or more times with the desired gas or gases, or both. These techniques may be used in conjunction with a protocol whereby the material is contained within a vessel prior to irradiation, and wherein the ambient air is purged from the vessel by flushing with the desired atmosphere components prior to irradiating the material.

The temperature at which the irradiation of the material comprising a biologically active agent occurs is preferably about 4° C. or lower. Preferably, the material and atmosphere are equilibrated to the desired temperature prior to irradiation and are maintained at a temperature constantly at or below about 4° C. during the irradiation process. The temperature at which irradiation occurs may be at or less than about 2° C., or may be at or less than about 0° C. If the material and atmosphere are equilibrated to a desired temperature prior to irradiation, the temperature at which equilibration occurs is preferably approximately equal to the temperature at which irradiation is performed.

Also provided are sterilized materials comprising a biologically-active agent, wherein said material exhibits substantially the same amount of biological activity as a non-sterilized control. The identity of the biologically active agent may be as described above with respect to the inventive methods. The amount of biological activity may be assessed according any appropriate assay. For example, the assay may comprise a cell proliferation assay, a transmigration assay, a angiogenesis assay, a cytotoxicity assay, a matrix deposition assay, a lymphocyte activation assay, an apoptosis assay, or any combination of such assays or other assay that is useful in assessing the biological activity in a sample. Those skilled in the art will recognize other assays that may be used to assess the biological activity of the material. "Assessing" the biological activity refers to measuring the degree of biological activity, or to determining the absence or presence of biological activity.

The inventive sterilized materials are preferably those which have been sterilized by irradiating the material with ionizing radiation at a dose of about 5 kGy to about 25 kGy while maintaining the material in an atmosphere comprising at least 95% by volume inert gas and at a temperature of about 4° C. or lower. The conditions of the irradiation, including the type and dose of radiation and the conditions, components, and temperature of the atmosphere are preferably as described above with respect to the inventive methods.

The present invention is further defined in the following examples. It should be understood that these examples, while indicating embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

EXAMPLE 1

Variation of Sterilization Factors in Sterilization of hUTC Lysate

An evaluation of a full factorial design of experiments was conducted to determine the optimal factor levels for the retention of hUTC lysate biological activity post-sterilization by gamma irradiation or e-beam methods. The sterilization factors tested included 1) sterilization in ambient air vs. nitrogen gas, 2) temperature during sterilization, and 3) irradiation dose. Collagen/oxidized regenerated cellulose (ORC) matrix containing lyophilized hUTC lysate and its respective non-lysate controls were irradiated under test conditions. Biological activity was measured using a mouse NIH/3T3 fibroblasts transwell proliferation assay.

Cell Growth and Harvest. Expanded human umbilical tissue derived cells were seeded at 5,000 cells per cm squared in gelatin-coated flasks with growth medium containing Dulbecco's Modified Eagles Media (DMEM)-low glucose, 15% fetal bovine serum (FBS), 1% penicillin/streptomycin (P/S), betamercaptoethanol (BME); these cells were expanded for 3 to 4 days (25,000 cells per cm squared target harvest density). Upon 70% confluency, the cells were harvested with trypsin, collected, and centrifuged at 300 rcf for 5 minutes. The trypsin/media was removed by aspiration and cells were washed three times with phosphate buffered saline (PBS).

Cell Wash and Aliquoting. After washing, the cells were re-suspended at 1.0E+07 cell/ml in PBS and delivered as 1 ml aliquots into 1.5 ml sterile siliconized micro-centrifuge tubes. The cells were centrifuged at 300 rcf for 5 minutes and the PBS was removed by aspiration.

Cell Lysis. Tubes containing cell pellets were immersed into liquid nitrogen ($LN_2$) for 60 seconds. The tubes were then removed from $LN_2$ and immediately immersed in a 37° C. water bath for 60 seconds or until thawed (3 min maximum incubation time). This process is repeated three times.

Centrifugation and Lysate Harvest. The freeze-thawed samples were centrifuged for 10 minutes at 13,000 rcf at 4° C. and placed on ice. The supernatant fluid from each tube was removed by pipette and transferred to a single sterile siliconized 1.5 ml tube. This process was repeated until no additional supernatant fluid could be recovered.

Fluid Volume Measurement. To approximate supernatant fluid volume, the tube containing 1.5 ml recovered supernatant fluid was weighed on a balance previously tared with an empty 1.5 ml micro-centrifuge tube (1 mg≈1 µl).

Protein Assay. To determine total protein content, 10 µl of lysate supernatant fluid was diluted into 990 µl PBS and further serially diluted in PBS. The dilution was analyzed by Bradford assay, or other equivalent protein assay (standard range 1.25-25 µg). This value was used to calculate the total protein per cell, the main metric used to ensure the consistency of the process.

Lysate Application and Lyophilization. Collagen/ORC samples (lot#1305263), pre-cut with a 3 mm biopsy punch, were aseptically placed into the wells of 48 well sterile, ultra low cluster cell culture dishes (Cat. No. 3473, Corning Inc., Corning, N.Y.). The supernatant fluid was applied to the material as single 150 µg total protein aliquots. Dishes containing test materials were loaded into the lyophilizer.

Lyophilization. Test materials with applied lysate and control materials without cell lysate were loaded into a FTS Systems Dura-Stop MP Stoppering Tray Dryer and lyophilized using the following ramping program. All steps had a ramping rate of 2.5° C./minute and a 100-mT vacuum (see Table 1, below).

TABLE 1

| Step | Shelf Temp (° C.) | Hold Time (min) |
| --- | --- | --- |
| a | −40 | 180 |
| b | −25 | 2160 |
| c | −15 | 180 |
| d | −5 | 180 |
| e | 5 | 120 |
| f | 20 | 120 |
| g | −20 | 60 |

After lyophilization, all samples were aseptically loaded into individual, sterile 1.5 ml screw-cap microfuge tubes (cat. no. 02-681-339, Fisher Scientific, Inc, Hampton, N.H.).

Experimental Design. A full-factorial design of experiments was constructed using MiniTab 14.0 to evaluate the gamma sterilization factors that affect hUTC lysate biological activity (see Table 2, below):

TABLE 2

Gamma Irradiation Design of Experiment

| Factor | Levels Tested |
| --- | --- |
| hUTC lysate | With, Without |
| Nitrogen Glove Box | With, Without |
| Dose (kGy) | 7, 12, 25 |
| Temperature (° C.) | 0, 4, 25 |

A second full-factorial design of experiments was constructed using MiniTab 14.0 to evaluate the e-beam sterilization factors that effect hUTC lysate biological activity. All materials were processed in nitrogen glove box and sterilized at 21° C. (see Table 3, below):

TABLE 3

Electron Beam Design of Experiment

| Factor | Levels Tested |
| --- | --- |
| hUTC lysate | With, Without |
| Dose (kGy) | 7, 12, 25 |

Table 4, below, provides the experimental run order for hUTC lysate treated collagen/ORC samples sterilized through gamma irradiation.

TABLE 4

Gamma Irradiation

| Run Order | Lysate Treatment | Glove Box Processing | Dose (kGy) | Temp (° C.) |
| --- | --- | --- | --- | --- |
| 1 | Without | With | 7 | 25 |
| 2 | With | Without | 25 | 25 |
| 3 | With | With | 25 | 25 |
| 4 | With | Without | 12 | 4 |
| 5 | Without | Without | 25 | 0 |
| 6 | Without | Without | 7 | 25 |
| 7 | With | With | 7 | 4 |
| 8 | Without | Without | 7 | 0 |
| 9 | With | Without | 7 | 0 |
| 10 | Without | With | 25 | 4 |
| 11 | Without | Without | 7 | 4 |
| 12 | Without | With | 12 | 25 |
| 13 | With | With | 7 | 0 |
| 14 | Without | Without | 12 | 4 |
| 15 | Without | With | 25 | 0 |
| 16 | Without | With | 7 | 0 |
| 17 | Without | Without | 12 | 0 |

TABLE 4-continued

Gamma Irradiation

| Run Order | Lysate Treatment | Glove Box Processing | Dose (kGy) | Temp (° C.) |
|---|---|---|---|---|
| 18 | With | Without | 12 | 25 |
| 19 | With | Without | 7 | 4 |
| 20 | With | With | 25 | 4 |
| 21 | With | Without | 7 | 25 |
| 22 | With | Without | 12 | 0 |
| 23 | Without | With | 12 | 0 |
| 24 | With | With | 7 | 25 |
| 25 | With | With | 25 | 0 |
| 26 | With | With | 12 | 4 |
| 27 | With | Without | 25 | 4 |
| 28 | Without | With | 25 | 25 |
| 29 | Without | With | 12 | 4 |
| 30 | With | Without | 25 | 0 |
| 31 | Without | Without | 25 | 4 |
| 32 | With | With | 12 | 0 |
| 33 | With | With | 12 | 25 |
| 34 | Without | Without | 12 | 25 |
| 35 | Without | With | 7 | 4 |
| 36 | Without | Without | 25 | 25 |

A set of collagen/ORC samples with or without hUTC lysate (n=6 each) was produced and stored at manufacturing facility at −80° C. during sterilization. A second "traveler" set of collagen/ORC samples with or without hUTC lysate (n=6 each) was produced to control for any effects sample shipment may have had on biological activity. This set was shipped with the irradiated samples and stored at gamma sterilization facility at 0° C. during. This set was returned with the irradiated samples for analysis.

Gamma Irradiation. Samples to be sterilized through gamma irradiation were delivered to the gamma sterilization facility on wet ice and stored at 0° C. until sorting and processing.

Samples marked for glovebox processing had the ambient air purged from their respective microfuge containers. The nitrogen purge was accomplished by placing samples into the antechamber of a low-oxygen, nitrogen flushed glovebox (Isolation Technologies, Model: Micro-Inert System 1.5×1, serial no. 5023A, manuf. date 4-94). The cycle designated as "01 ONE CYCLE" was executed prior to bringing samples into the main chamber. This cycle consists of a series of four evacuations, followed by back-flushing with nitrogen to standard atmospheric pressure. The evacuations occur for five minutes, reaching a pressure less than 10 torr. Samples were then transferred into the main chamber to equilibrate. After approximately one hour, their caps, which had been loosened prior to the evacuation cycles, were tightened, and the samples were removed from the glovebox. After the nitrogen purge, these samples were stored at −70° C.

Prior to gamma irradiation, samples were removed from the −70° C. and allowed to equilibrate to room temperature for approximately 30 minutes. During gamma irradiation, the temperature was monitored using an Omega RD-MV 112 Paperless Recorder (S/N S5D803918). The temperature was adjusted to within ±2° C. of the requested set point and controlled manually via a Model 328 Vortex Tube cooler. The radiation cycle was initiated, and the airflow adjusted to maintain and control the temperature. Materials were irradiated with a Gammacell 220 using a cobalt-60 isotope.

E-Beam Irradiation. Samples for e-beam irradiation were delivered to the gamma sterilization facility on wet ice. Samples were purged of ambient air in a nitrogen glovebox, as previously described. After processing, all samples were shipped to the e-beam sterilization facility on dry ice. Six empty microfuge tubes were also sent to calibrate for dose penetration.

E-beam sterilization was performed with a Linac electron beam irradiator. Briefly, the samples were placed in respective treatment boxes containing dry ice. The boxes were passed in front of the scanning horn by conveyor and irradiated by the electron beam. The beam current was held constant, and the speed of the conveyor was adjusted to deliver the requested dose.

Traveler Control. The traveler control set were not subjected to irradiation. These samples were stored at the gamma sterilization facility at −70° C. until the completion of all sterilization cycles. Upon completion of all irradiation cycles, the traveler set was returned to its source with all other samples.

Mouse Fibroblasts. Mouse NIH/3T3 fibroblasts (ATCC CRL-1658) were expanded in growth media (DMEM high glucose with 10% fetal calf serum and 1% penicillin/streptomycin).

Transwell Assay. The mouse NIH/3T3 fibroblasts were plated into the lower portion of a 96 well transwell plate (Cat. No. 3381, Corning Inc., Corning, N.Y.) at 2,500 cells per well and cultured overnight. Media was removed by aspiration and the appropriate media (150 µl per well, 50 µl per transwell) was added, followed by treatments. Positive controls were NIH/3T3 cells in 10% NCS and empty transwell. Negative controls were NIH/3T3 cells in 1% NCS and empty transwell. All test conditions were cultured in 1% NCS.

Cell Harvest and Analysis. On day 4, cells in transwells were harvested by trypsinization (75 µl trypsin followed with 75 µl complete media to neutralize trypsin) and 50 µl of staining solution (48:1:1 media, DMSO, Guava ViaCount Flex reagent (Cat. No. 4500-0110, Guava Technologies, Hayward, Calif.)) was added to each well. Cells were counted using a Guava EasyCyte instrument (Guava Technologies, Hayward, Calif.) with an original volume of 0.2 ml and dilution factor of one.

Results. Table 5, below, provides the results of the measurement of average cells per well for each gamma irradiated condition, as determined by Guava EasyCyte and Guava ViaCount Flex reagent. Condition code refers to samples of collagen/ORC that were subjected to the same conditions, differing only in the treatment with hUTC lysate.

TABLE 5

Gamma Irradiation

| Condition Code | Run Order | Lysate Treatment | Glove Box Processing | Dose (kGy) | Temp (° C.) | Average (Cells/Well) | Std. Dev. |
|---|---|---|---|---|---|---|---|
| A | 13 | With | With | 7 | 0 | 41,053.73 | 11,450.09 |
|   | 16 | Without | With | 7 | 0 | 16,782.78 | 4,269.39 |
| B | 7 | With | With | 7 | 4 | 22,658.34 | 8,513.94 |
|   | 35 | Without | With | 7 | 4 | 11,930.00 | 1,647.71 |

TABLE 5-continued

Gamma Irradiation

| Condition Code | Run Order | Lysate Treatment | Glove Box Processing | Dose (kGy) | Temp (° C.) | Average (Cells/Well) | Std. Dev. |
|---|---|---|---|---|---|---|---|
| C | 24 | With | With | 7 | 25 | 27,393.44 | 6,677.86 |
|  | 1 | Without | With | 7 | 25 | 12,479.81 | 3,724.32 |
| D | 32 | With | With | 12 | 0 | 26,715.72 | 8,810.56 |
|  | 23 | Without | With | 12 | 0 | 18,387.29 | 5,916.10 |
| E | 26 | With | With | 12 | 4 | 35,589.61 | 9,530.70 |
|  | 29 | Without | With | 12 | 4 | 14,208.16 | 2,971.11 |
| F | 33 | With | With | 12 | 25 | 23,660.07 | 9,301.86 |
|  | 12 | Without | With | 12 | 25 | 13,680.73 | 3,682.22 |
| G | 25 | With | With | 25 | 0 | 39,387.61 | 15,636.45 |
|  | 15 | Without | With | 25 | 0 | 18,661.71 | 4,498.87 |
| H | 20 | With | With | 25 | 4 | 23,981.00 | 7,604.69 |
|  | 10 | Without | With | 25 | 4 | 12,817.93 | 6,256.35 |
| I | 3 | With | With | 25 | 25 | 14,811.75 | 6,384.01 |
|  | 28 | Without | With | 25 | 25 | 19,408.52 | 6,223.30 |
| J | 9 | With | Without | 7 | 0 | 18,069.07 | 6,326.40 |
|  | 8 | Without | Without | 7 | 0 | 23,331.11 | 4,729.10 |
| K | 19 | With | Without | 7 | 4 | 32,693.02 | 15,711.67 |
|  | 11 | Without | Without | 7 | 4 | 11,794.49 | 978.07 |
| L | 21 | With | Without | 7 | 25 | 27,495.82 | 8,075.72 |
|  | 6 | Without | Without | 7 | 25 | 10,729.76 | 2,381.61 |
| M | 22 | With | Without | 12 | 0 | 27,755.70 | 12,084.05 |
|  | 17 | Without | Without | 12 | 0 | 19,870.94 | 2,999.99 |
| N | 4 | With | Without | 12 | 4 | 16,613.38 | 6,319.08 |
|  | 14 | Without | Without | 12 | 4 | 6,040.50 | 950.71 |
| O | 18 | With | Without | 12 | 25 | 9,756.47 | 6,344.04 |
|  | 34 | Without | Without | 12 | 25 | 11,958.15 | 1,573.89 |
| P | 30 | With | Without | 25 | 0 | 6,306.70 | 2,485.10 |
|  | 5 | Without | Without | 25 | 0 | 18,179.73 | 3,669.78 |
| Q | 27 | With | Without | 25 | 4 | 13,374.71 | 6,142.68 |
|  | 31 | Without | Without | 25 | 4 | 13,531.81 | 1,842.50 |
| R | 2 | With | Without | 25 | 25 | 3,891.18 | 562.15 |
|  | 36 | Without | Without | 25 | 25 | 10,904.23 | 2,768.38 |

Table 6, below, provides the results of the measurement of average cells per well for each e-beamed sterilized condition, as determined by Guava EasyCyte and Guava ViaCount Flex reagent. Condition code refers to samples of collagen/ORC that were subjected to the same conditions, differing only in the treatment with hUTC lysate.

TABLE 6

E-Beam

| Condition Code | Run Order | Lysate Treatment | Glove Box Processing | Dose (kGy) | Average (Cells/Well) | Std. Dev. |
|---|---|---|---|---|---|---|
| A | 1 | With | With | 7 | 65,452.02 | 10,316.12 |
|  | 4 | Without | With | 7 | 28,025.00 | 3,077.64 |
| B | 2 | With | With | 12 | 63,743.84 | 8,664.52 |
|  | 5 | Without | With | 12 | 32,579.22 | 6,942.06 |
| C | 3 | With | With | 25 | 55,177.92 | 10,457.69 |
|  | 6 | Without | With | 25 | 32,080.82 | 13,634.10 |
| Traveler | Treated |  |  |  | 49,337.37 | 12,349.89 |
|  | Untreated |  |  |  | 18,220.36 | 4,289.74 |
| In-House | Treated |  |  |  | 71,417.83 | 13,972.36 |
|  | Untreated |  |  |  | 37,303.30 | 7,994.61 |

Figure 2:
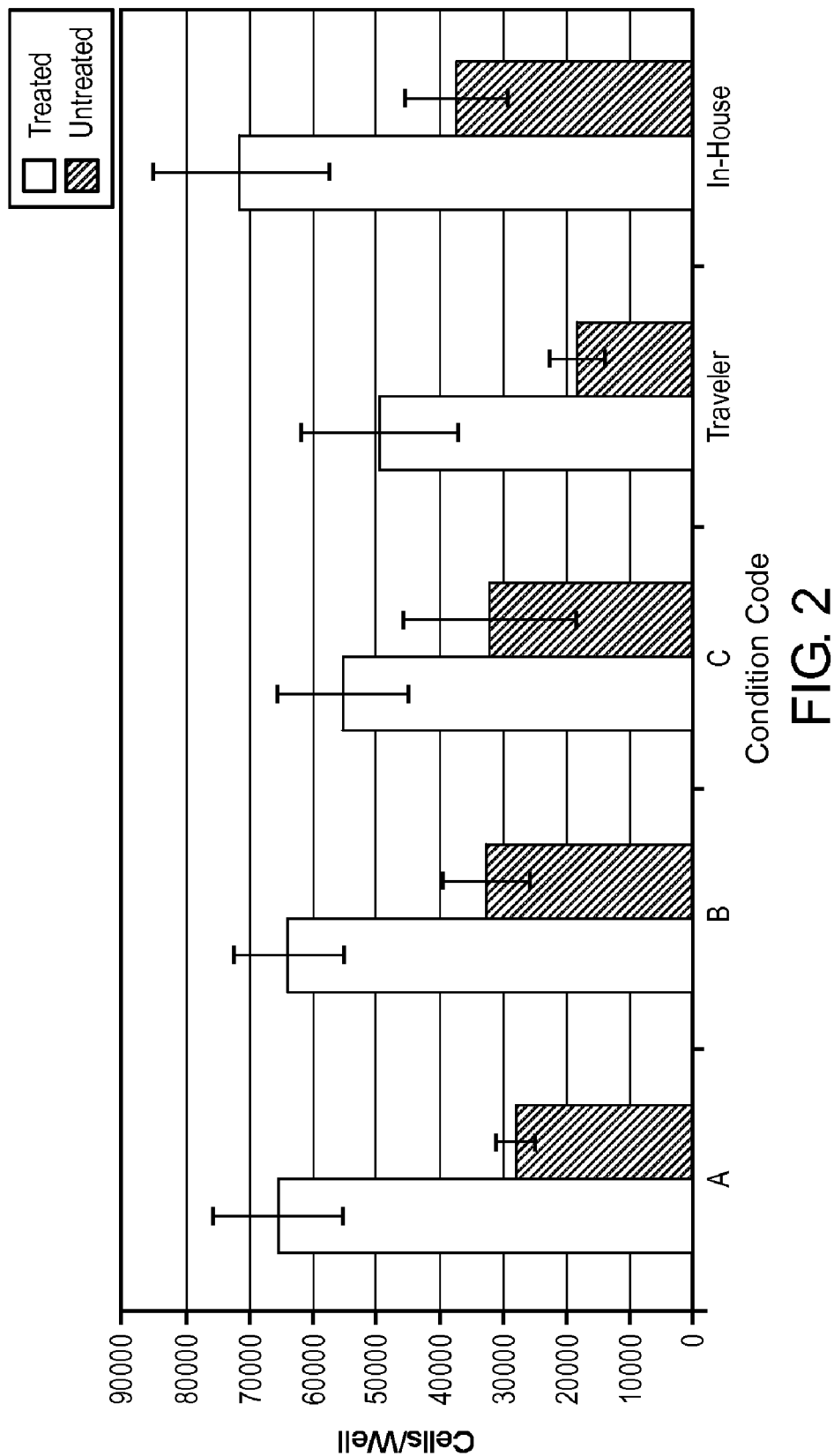
FIG. 2 depicts the measured average quantity of average cells per well of NIH/3T3 mouse fibroblasts co-cultured with electron beam-irradiated collagen/ORC samples that are either treated with 150 μg hUTC lysate protein or left untreated.
Figure 3:
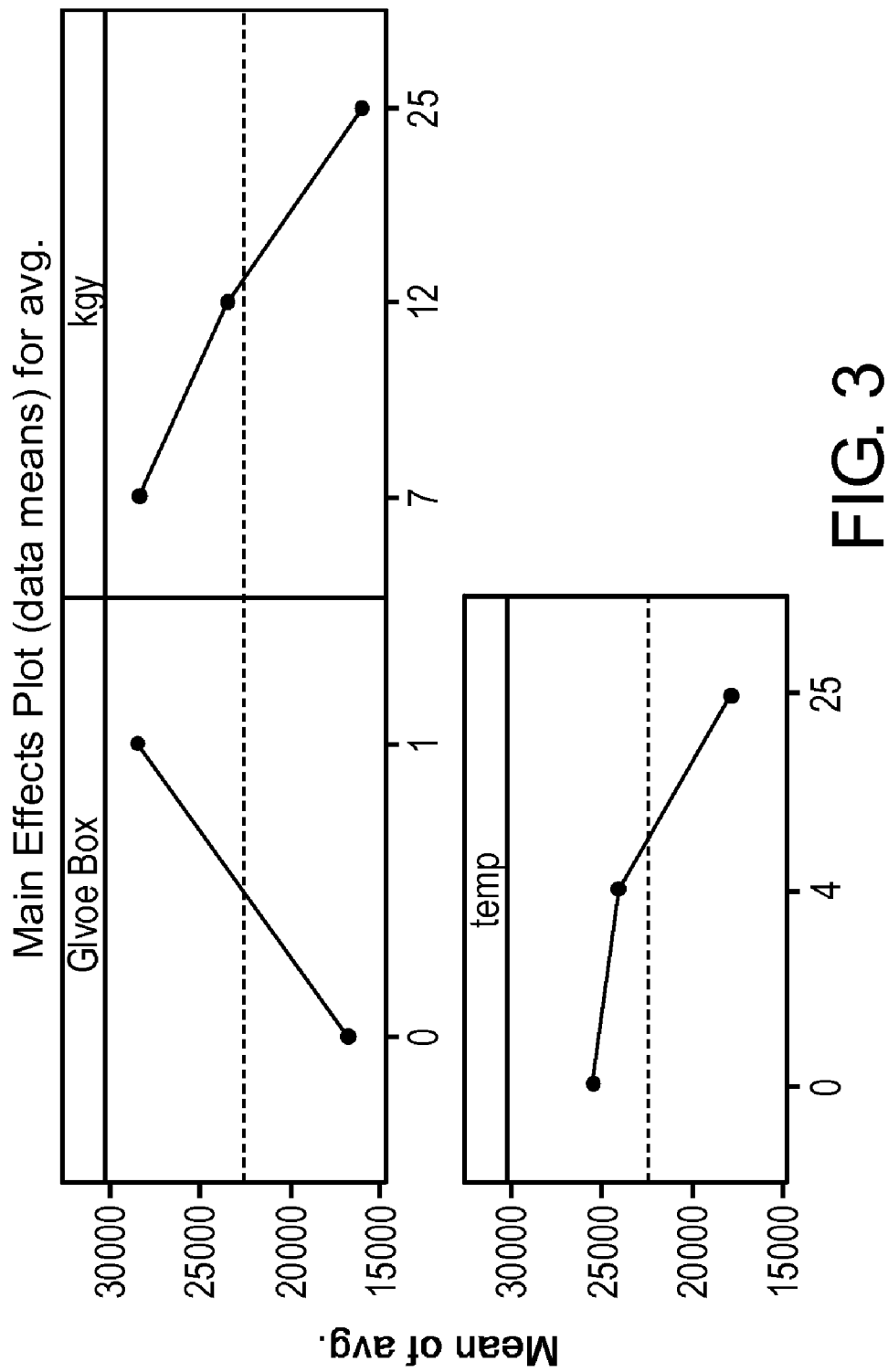
FIG. 3 provides main effects plots for each of the three variable conditions used in the present study.

FIG. 1 provides the results of the measurement of average cells/well of NIH/3T3 mouse fibroblasts co-cultured with gamma irradiated collagen/ORC samples either treated with 150 µg hUTC lysate protein or untreated and controls. Condition codes are provided in Table 5. FIG. 2 provides the results of the measurement of average cells/well of NIH/3T3 mouse fibroblasts co-cultured with electron beam sterilized collagen/ORC samples either treated with 150 µg hUTC lysate protein or untreated and controls. Condition codes are provided in Table 6. FIG. 3 provides main effects plots for each of the three variable conditions used in the present study.

Biological activity was maintained in approximately 72% of gamma irradiated hUTC lysate containing collagen/ORC samples as compared to collagen/ORC samples alone regardless of test conditions. Samples sterilized at 7 kGy at 0° C. in nitrogen retained the most biological activity and no significant difference was noted between the lysate containing sample and the non-irradiated lysate control. There was a correlation between sterilization in nitrogen, low temperature, and low irradiation dose and lysate biological activity as demonstrated by cell proliferation.

The lysates' biological activity was also maintained in all e-beam irradiated hUTC lysate containing collagen/ORC samples. The lysate containing samples sterilized at 7 kGy retained the most biological activity and no significant difference was noted between the 7 and 25 kGy treated lysate containing samples and the non-irradiated lysate containing traveler control.

EXAMPLE 2

Characterization of Gamma-Ray Sterilized hUTC Cell Lysate by SDS-PAGE

The signature banding-pattern of the major proteins present in hUTC lysate was compared among various sterilization protocols by use of sodium dodecylsulfate polyacrylamide gel electrophoresis (SDS-PAGE).

Lysate was prepared by repeated freeze/thaw cycles of hUTC cell pellets, followed by centrifugation. Samples were then prepared and labeled according to the treatment groups listed in Table 7, below:

TABLE 7

| Group | Test condition | Lot/Expiration | Treatment |
|---|---|---|---|
|  | SURGICEL FIBRILLAR ™ Absorbable Hemostat (SCF) | UGB325-1, expiration February 2008 |  |
|  | PROMOGRAN ™ Matrix (PGM) | 1305263, expiration May 2007 |  |
| A | VICRYL ™ (polyglactin 910) nonwoven (VNW) without lysate (VNW) | ID: 5248-46-1 thickness 0.50 mm density 65.2) | Control |
| B | Lysate lyophilized on VNW | ID: 5248-46-1 thickness 0.50 mm density 65.2) | Test group |
| 1C | Pre-lyophilized lysate (P) |  | Control |
| 2C | Post-lyophilized powdered lysate |  | Control |
| 3C | Post-lyophilized powdered lysate loaded onto VNW |  | Control (not transported to SST) |

Protein content measurements were conducted, using the Quick Start Bradford Protein Assay (BioRad, Cat. #500-0205). This assay has a reported linear range of 1.25-10 µg/ml in the microassay format and is based on Coomassie Brilliant Blue G-250 dye shifts in absorbance due to protein binding.

For SDS-PAGE, the Invitrogen NOVEX® Pre-cast gel system was utilized. A Tris-Glycine 4% stacking, 4-20% gradient separating gel was used due to its ability to separate a wide molecular weight range of molecules (Invitrogen, Cat. #E660252BOX). For studies conducted at CBAT, the BenchMark™ 10-220 kDa Protein Ladder (Invitrogen, Cat. #10747-012) was used as a reference. Samples were analyzed in reducing conditions according to the supplied manufacturer's instructions (Invitrogen XCell SureLock™ Mini-Cell, Version H; August 20, Catalog Nos. EI0001, EI0020, and EI0002; NOVEX® Tris-Glycine Gels, Catalog no. IM-6000F).

Running the gel. A 1× Tris-Glycine SDS Running Buffer was prepared by adding 100 ml of 10× NOVEX® Tris-Glycine SDS Running Buffer (Invitrogen, Cat. #LC2675) to 900 ml deionized water. The gel chamber was filled with the prepared 1× Tris-Glycine SDS Running Buffer. The appropriate concentration and volume of the protein sample was loaded onto the gel. The gel was run using the following conditions:

| | |
|---|---|
| Voltage: | 125 V constant |
| Run Time: | 90 minutes |
| Expected Current: | 30-40 mA/gel (start); 8-12 mA/gel (end) |

Staining and drying the gel. Gels were stained using the Invitrogen SIMPLYBLUE™ SafeStain (Invitrogen, Cat. #LC6060) following the supplied manufacturer's instructions (Basic Protocol). After staining, the gel was dried using the DRYEASE® Mini-Gel Drying System (Invitrogen, Cat. #N12387) according the supplied manufacturer's instructions.

Extraction of lysate proteins from scaffolds. To extract the proteins from scaffolds for analysis, materials were incubated in 1 ml of PBS overnight with shaking at 4° C.

Initial studies were conducted to assess the protein-banding pattern of hUTC lysate, as analyzed by SDS-PAGE to determine the hUTC "protein signature". Powdered lyophilized lysate (L042205) was dissolved in dH$_2$O to a final concentration of 0.5 µg/µl. Lysate was added to the sample buffer and reducing agent, and heated as described. The lysate+VNW combination was placed in 120 µl of sample buffer with reducing agent and water, then heated and loaded onto the gel as described. Lastly, a sample of basic-FGF was prepared as described as a control.

Following the initial characterization of hUTC lysate, gel electrophoresis was performed to determine the utility of this method to detect changes in protein banding pattern post processing. In these studies, protein-banding pattern was evaluated pre and post lyophilization of the hUTC lysate. In addition, these studies assessed whether hUTC lysate proteins could be assayed after lyophilization onto scaffolds other than VNW (e.g., SCF and PGM).

The scaffold samples were prepared by being placed in a 100 µl mixture of sample buffer, reducing agent and water, then heated as previously described; 17 µl (5 µg) of each sample was loaded onto the gel. The powdered samples and the pre-lyophilized liquid were dissolved in water to a final concentration of 2 µg/µl and prepared for loading as described in the XCell SURELOCK™ Mini-Cell manufacturer's instructions; the final amount of protein loaded onto the gel was 5 µg.

Assay validation studies were conducted. The Invitrogen gel system was used to replicate the system used at CBAT. An extraction step, described in the materials and methods, was added to the previously described protocol to elute lysate from the lyophilized scaffold. VNW scaffolds without lysate were used as a control.

Studies were also conducted to determine stability of hUTC lysate after lyophilization. The powdered and pre-lyophilized samples were dissolved in PBS before being loaded onto the gels, as previously described.

Lysate characterization post-processing (sterilization). Sixteen different sterilization protocols were assessed (see Table 8, below) with four samples tested per condition.

TABLE 8

Matrix Design for Sterilization of Lysate/VNW Samples

| Dose (kGy) | Temperature (° C.) | Atmosphere | Sample ID |
|---|---|---|---|
| 0 | 25 | Nitrogen | 1 |
| 0 | 25 | Air | 2 |
| 0 | −70 | Nitrogen | 3 |
| 0 | −70 | Air | 4 |
| 7 | 25 | Nitrogen | 5 |

TABLE 8-continued

Matrix Design for Sterilization of Lysate/VNW Samples

| Dose (kGy) | Temperature (° C.) | Atmosphere | Sample ID |
|---|---|---|---|
| 7 | 25 | Air | 6 |
| 7 | −70 | Nitrogen | 7 |
| 7 | −70 | Air | 8 |
| 14 | 25 | Nitrogen | 9 |
| 14 | 25 | Air | 10 |
| 14 | −70 | Nitrogen | 11 |
| 14 | −70 | Air | 12 |
| 25 | 25 | Nitrogen | 13 |
| 25 | 25 | Air | 14 |
| 25 | −70 | Nitrogen | 15 |
| 25 | −70 | Air | 16 |

Lysate tested in this assay was from the same lot. Samples were sterilized by gamma irradiation. After sterilization, sample Groups A, B and C were analyzed. Additional lots of lysate (L051305 powder and VNW scaffolds, L040405 powder and L042205 powder) were sent for comparison. Samples of VNW containing lysate were extracted using the method previously described. Controls included pre-lyophilized lysate, lysate post-lyophilization, L092605 as a powder (2C) and loaded onto a VNW scaffold (3C). Sample 3C was not irradiated and remained at the inventors' location as a control.

Figure 4:
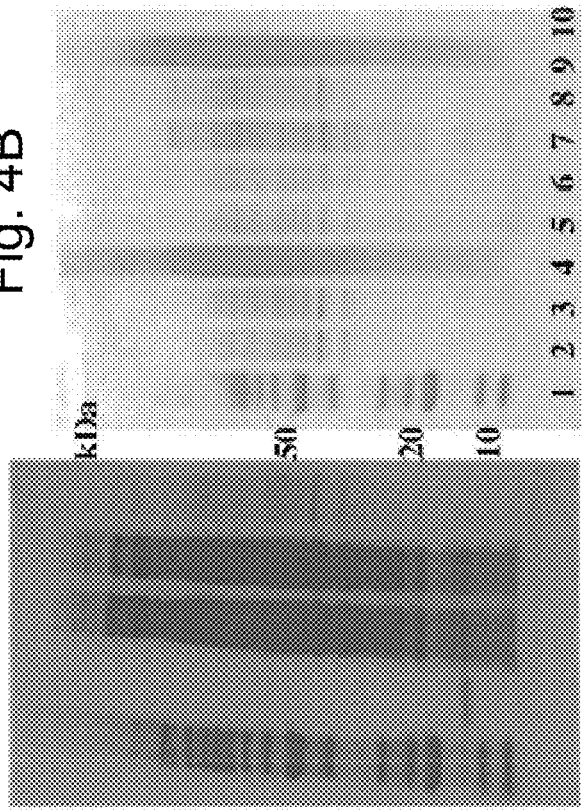
FIGS. 4A and 4B provide an SDS-PAGE analysis of data generated in accordance with a characterization of hUTC lysate pre-processing.

Results. SDS-PAGE data demonstrated that discrete bands were observed in hUTC lysate. When hUTC lysate was compared in samples extracted from VNW scaffolds to the lyophilized lysate powder, the identical core-banding pattern was observed. In addition, when comparing results between lots of hUTC lysate (L042205 and L051305), similar results were observed; FIG. 4A depicts the results of testing two samples of lysate, L042205 as a lyophilized powder and L051305 after lyophilization onto a scaffold (30 μg/scaffold). Lanes were loaded as follows: 1) 7 μl of the BenchMark™ Protein Ladder, 2) 20 μl (500 ng) of basic-FGF, 3 & 4) L051305 20 μl (5 μg) and 15 μl (3.75 μg) respectively, and lastly 5) μl of L042205 (μg).

Further characterization of post-production processing is shown in FIG. 4B. The gel was loaded in the following order: (1) BENCHMARK™ Protein Ladder, (2) L061305 powder, (3) L061305 on VNW, (4) L061305 on PGM, (5) L062405P, (6) L062405 powder, (7) L062405 on VNW, (8) L062405 on SCF, (9) PGM scaffold without lysate and (10) SCF scaffold without lysate. Multiple lots of lysate were examined (lots L061305 and L062405) before and after lyophilization. Banding patterns of hUTC lysate were consistent before lyophilization (lane 5), and after lyophilization as a powder (lanes 2 and 6). In addition, lysate extracted from VNW scaffolds (lanes 3 and 7) showed consistent results. These data show that a consistent banding pattern was observed for all conditions tested.

Gel results (FIG. 4B) also examined the banding pattern of lysate after lyophilization onto two other types of scaffolds, SURGICEL FIBRILLAR™ (SCF) and PROMOGRAN™ Matrix (PGM). Lane 8 shows lysate (L062405) after extraction from the SCF scaffold with lane 10 as a comparison (control scaffold without lysate). The results yielded a lysate banding pattern that is consistent with lysate banding pattern observed previously in this report. By contrast, results from PGM scaffolds (lanes 4 and 9), show that collagen component of this collagen/ORC scaffold yields a gel with unresolved bands.

Figure 5:
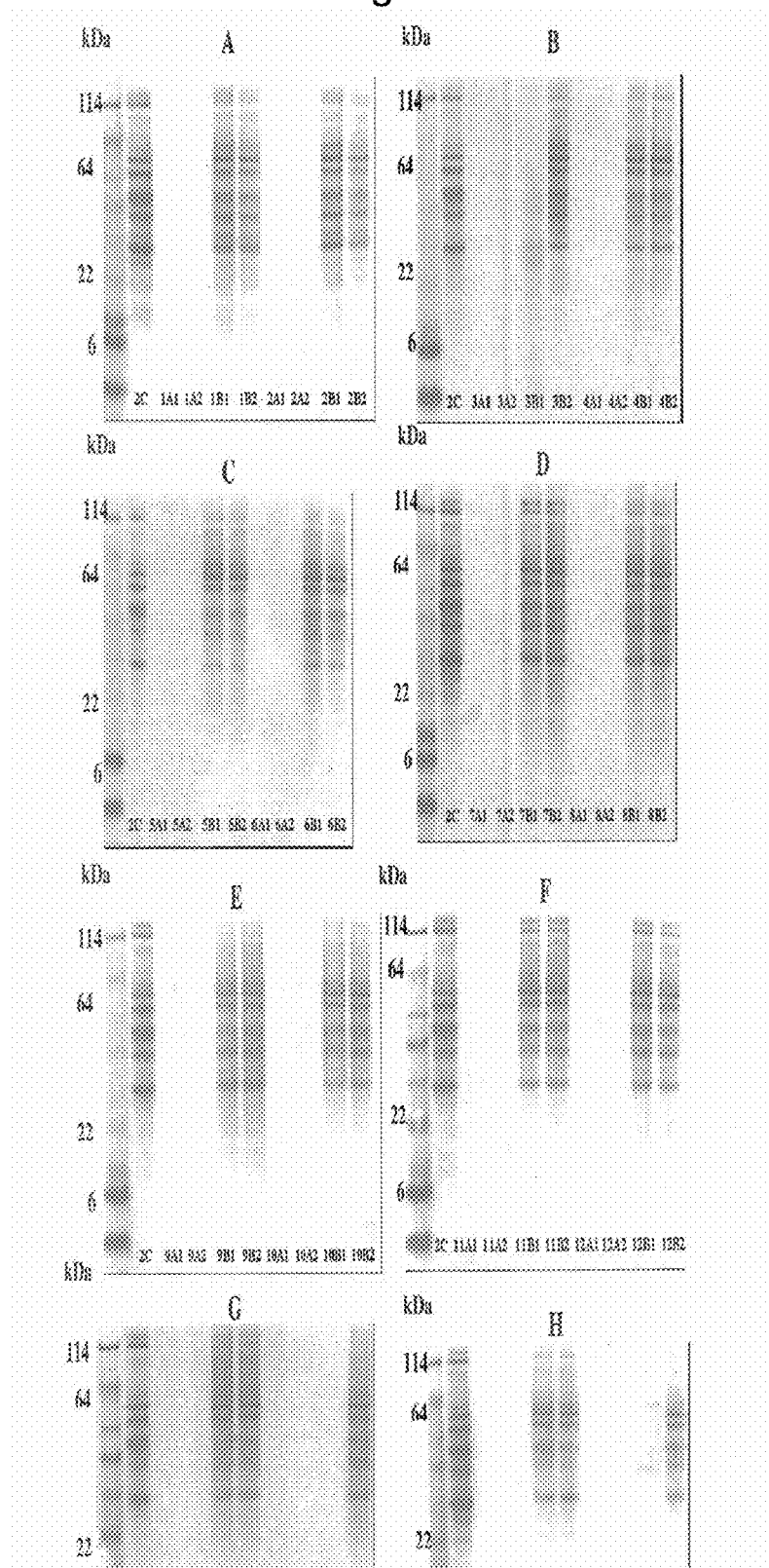
FIG. 5 details the results of SDS-PAGE analysis in order to determine the effects of sterilization conditions.

FIG. 5 details the SDS-PAGE analysis of the sterilization study conducted at Lofstrand determining the effects of sterilization conditions outlined in Table 8, supra. FIG. 5 shows the results obtained from the SDS-PAGE analysis. Bradford data (not shown) revealed that little or no proteins were extracted from sample 14B1 and 16B1 (FIG. 5G). At high doses of irradiation, (samples 15B1, 15B2 and 16B2) hUTC lysate retained the characteristic banding-pattern (FIG. 5H). Samples are coded on the gels according to the following scheme: XYZ (e.g., 3A1) where X=Sample ID in Table 8, Y=Treatment codes in Table 7, and Z=sample replicate number. Sample 2C was loaded onto each gel to standardize data.

Bradford data (see Table 9, below) revealed that no proteins were extracted from sample 14B1. Bradford protein content results show inconsistency of protein recovery with the current Bradford method. Despite these differences in protein loading, at high doses of irradiation, (samples 15B1, 15B2 and 16B2) the lysate retained the characteristic banding-pattern.

Table 9, below, depicts Bradford protein concentration assay data for hUTC lysate on 90/10 PGA/PLA scaffolds post-sterilization by gamma irradiation, as performed by Lofstrand Labs Ltd. Samples are coded according to the following scheme: XYZ (e.g., 3A1) where X=Sample ID in Table 8, Y=Treatment codes in Table 7, and Z=sample replicate number. Sample 2C was loaded onto each gel to standardize data. Results from this study show inconsistency of protein recovery with the current Bradford method.

TABLE 9

| | Initial | | Repeat | | |
|---|---|---|---|---|---|
| Sample ID | [Protein] (μg/μl) | Recovered (μg) | [Protein] (μg/μl) | Recovered (μg) | Difference (%) |
| 1C | 4.05 | 238.50 | 219.8 | 87.9 | 22 |
| 2C | 5.62 | 281.50 | 174 | 68.8 | 38 |
| 3C | 0.65 | 22.75 | 14.77 | 49.2 | 35 |
| 1B-1 | 1.17 | 58.50 | | | |
| 1B-2 | 1.35 | 67.50 | | | |
| 2B-1 | 1.17 | 58.50 | | | |
| 2B-2 | 1.68 | 58.80 | | | |
| 3B-1 | 1.00 | 50.00 | 0.13 | 6.50 | 87 |
| 3B-2 | 1.37 | 54.80 | 1.00 | 40.00 | 27 |
| 4B-1 | 1.22 | 61.00 | 0.80 | 40.00 | 34 |
| 4B-2 | 1.32 | 72.60 | 0.93 | 51.15 | 29.5 |
| 5B-1 | 1.19 | 65.45 | 0.78 | 42.90 | 34.0 |
| 5B-2 | 1.12 | 50.40 | 0.81 | 36.45 | 27.5 |
| 6B-1 | 0.66 | 33.00 | 0.38 | 19.00 | 42.0 |
| 6B-2 | 1.14 | 62.70 | 0.72 | 39.60 | 36.0 |
| 7B-1 | 1.10 | 60.50 | 0.71 | 39.05 | 35.5 |
| 7B-2 | 1.24 | 68.20 | 0.78 | 42.90 | 37.0 |
| 8B-1 | 1.30 | 78.00 | 0.84 | 50.40 | 35.0 |
| 8B-2 | 1.35 | 78.30 | 0.93 | 53.94 | 31.0 |
| 9B-1 | 1.10 | 60.50 | 0.26 | 14.30 | 76.0 |
| 9B-2 | 1.21 | 72.60 | 0.92 | 55.20 | 24.0 |
| 10B-1 | 1.03 | 56.65 | 0.57 | 31.35 | 44.0 |
| 10B-2 | 1.04 | 60.32 | 0.74 | 42.92 | 28.8 |
| 11B-1 | 1.35 | 81.00 | 1.02 | 61.20 | 24.0 |
| 11B-2 | 1.07 | 64.20 | 0.82 | 49.20 | 23.0 |
| 12-B-1 | 1.25 | 72.50 | 0.89 | 51.62 | 28.8 |
| 12-B-2 | 1.28 | 70.40 | 0.98 | 53.90 | 23.0 |
| 13B-1 | 1.10 | 60.50 | 0.66 | 36.30 | 40.0 |
| 13B-2 | 1.17 | 64.35 | 0.70 | 38.50 | 40.0 |
| 14B-1 | 1.02 | 0.91 | 0.00 | 0.00 | 100.0 |
| 14B-2 | 1.24 | 68.20 | 0.81 | 44.55 | 34.6 |
| 15B-1 | 0.64 | 34.98 | 0.41 | 22.55 | 35.5 |
| 15B-2 | 0.93 | 53.12 | 0.73 | 41.61 | 21.7 |
| 16B-1 | 0.92 | 50.38 | 0.03 | 1.65 | 96.7 |
| 16B-2 | 0.79 | 43.18 | 0.54 | 29.70 | 31.2 |

This data indicates that hUTC lysate has a consistent banding pattern that can be used as an in vitro method to demonstrate lot-to-lot equivalency of lysate, as well as lysate stability post processing. In addition, this characteristic-banding pattern was not significantly altered by gamma sterilization.

hUTC lysate signature banding pattern consisted of five to six bands present at 158.4, 96.3, 87.3, 69.1, 58.3 and 43.3 kd. SDS-PAGE can reliably detect protein-banding pattern of hUTC lysate that has been loaded onto and extracted from nonwoven scaffolds made from VICRYL™ (polyglactin 910) nonwoven fibers.

The disclosures of each patent, patent application and publication cited or described in this document are hereby incorporated herein by reference, in their entirety.

What is claimed:

1. A method for sterilizing a material comprising a biologically-active agent without the addition of a stabilizer or removal of solvent, and without substantial loss in biological activity comprising:
   sterilizing said material by irradiating said material with ionizing radiation at a dose of about 5 kGy to about 25 kGy while maintaining said material in an atmosphere comprising at least 95% by volume inert gas and at a temperature of about 4° C. or lower, without adding a stabilizer or removing solvent prior to irradiation, wherein said material retains its biological activity after sterilization.

2. The method according to claim 1 wherein said ionizing radiation comprises X-rays, gamma radiation, or electron beams.

3. The method according to claim 1 wherein said dose of ionizing radiation is about 6 kGy to about 12 kGy.

4. The method according to claim 1 wherein said dose of ionizing radiation is about 7 kGy.

5. The method according to claim 1 wherein said inert gas comprises nitrogen.

6. The method according to claim 1 wherein said atmosphere comprises about 100% by volume nitrogen.

7. The method according to claim 1 wherein said temperature is about 0° C.

8. The method according to claim 1, wherein said material is contained within a vessel, and wherein said method further comprises purging the ambient air from said vessel by flushing with said inert gas prior to irradiating said material.

9. The method according to claim 1 wherein said biologically active agent comprises cells, cell derivatives, growth factors, or any combination thereof.

10. The method according to claim 1 wherein said biologically active agent is selected from the group consisting of epithelial cells, bone marrow cells, adipocytes, stem cells, keratinocytes, melanocytes, dermal fibroblasts, keratinocytes, vascular endothelial cells, myoblasts, myocytes, hepatocytes, smooth muscle cells, striated muscle cells, stromal cells, other soft tissue cells or progenitor cells, chondrocytes, osteoblasts, islet cells, nerve cells, placenta-derived cells, human umbilical tissue derived cells (hUTC), human kidney derived cells, or any combination thereof.

11. The method according to claim 1 wherein said biologically active agent comprises a cell derivative selected from the group consisting of cell lysate, trophic factors, growth factors, cytokines, conditioned media, or any combination thereof.

12. The method according to claim 1 wherein said biologically active agent comprises hUTC lysate.

13. The method according to claim 1 wherein said biologically active agent comprises a growth factor selected from the group consisting of PDGF-BB, bFGF, TGF-beta, HGF, VEGF, GDF-5, or any combination thereof.

14. The method according to claim 1 wherein said material further comprises a scaffold composition.

15. The method according to claim 14 wherein said scaffold composition comprises collagen, cellulose, fibrin, elastin, gelatin, demineralized bone, hyaluronic acid, poly(lactic acid), poly(glycolic acid), polycaprolactone, polyanhydrides, polyhydroxybutyrates, or any combination thereof.

16. The method according to claim 1 wherein said amount of biological activity is assessed according to a cell proliferation assay, transmigration assay, angiogenesis assay, cytotoxicity assay, matrix deposition assay, lymphocyte activation assay, or apoptosis assay.

17. A method for sterilizing a material comprising a biologically-active agent consisting essentially of sterilizing said material by irradiating said material with ionizing radiation at a dose of about 5 kGy to about 25 kGy while maintaining said material in an atmosphere comprising at least 95% by volume inert gas and at a temperature of about 4° C. or lower, wherein said material retains its biological activity after sterilization.

18. The method according to claim 17 wherein said ionizing radiation comprises X-rays, gamma radiation, or electron beams.

19. The method according to claim 17 wherein said dose of ionizing radiation is about 6 kGy to about 12 kGy.

20. The method according to claim 17 wherein said inert gas comprises nitrogen.

21. The method according to claim 17 wherein said atmosphere comprises about 100% by volume nitrogen.

22. The method according to claim 17 wherein said biologically active agent is selected from the group consisting of epithelial cells, bone marrow cells, adipocytes, stem cells, keratinocytes, melanocytes, dermal fibroblasts, keratinocytes, vascular endothelial cells, myoblasts, myocytes, hepatocytes, smooth muscle cells, striated muscle cells, stromal cells, other soft tissue cells or progenitor cells, chondrocytes, osteoblasts, islet cells, nerve cells, placenta-derived cells, human umbilical tissue derived cells (hUTC), human kidney derived cells, or any combination thereof.

23. The method according to claim 17 wherein said biologically active agent comprises a cell derivative selected from the group consisting of cell lysate, trophic factors, growth factors, cytokines, conditioned media, or any combination thereof.

24. The method according to claim 17 wherein said biologically active agent comprises hUTC lysate.

25. The method according to claim 17 wherein said biologically active agent comprises a growth factor selected from the group consisting of PDGF-BB, bFGF, TGF-beta, HGF, VEGF, GDF-5, or any combination thereof.

26. The method according to claim 17 wherein said material further comprises a scaffold composition.

27. The method according to claim 26 wherein said scaffold composition comprises collagen, cellulose, fibrin, elastin, gelatin, demineralized bone, hyaluronic acid, poly(lactic acid), poly(glycolic acid), polycaprolactone, polyanhydrides, polyhydroxybutyrates, or any combination thereof.

28. A method for sterilizing a material comprising a biologically-active agent consisting of sterilizing said material by irradiating said material with ionizing radiation at a dose of about 5 kGy to about 25 kGy while maintaining said material in an atmosphere comprising at least 95% by volume inert gas and at a temperature of about 4° C. or lower, wherein said material retains its biological activity after sterilization.

* * * * *